United States Patent [19]

Sakai et al.

[11] Patent Number: 5,579,354
[45] Date of Patent: Nov. 26, 1996

[54] METHOD OF MEASURING A CORROSION POTENTIAL, METHOD OF SIMULATING POTENTIAL CHARACTERISTICS OF A REACTION RATE, AND PLANT MONITORING SYSTEM ADOPTING THEM

[75] Inventors: Masanori Sakai, Hitachiota; Noriyuki Ohnaka, Katsuta; Takahashi Takuya; Yamauchi Hiroshi, both of Hitachi, all of Japan

[73] Assignee: Hitachi, Ltd., Tokyo, Japan

[21] Appl. No.: 359,362

[22] Filed: Dec. 20, 1994

[30] Foreign Application Priority Data

Dec. 20, 1993 [JP] Japan .................................. 5-320517

[51] Int. Cl.$^6$ .................................................. G21C 17/00
[52] U.S. Cl. ........................ 376/245; 376/305; 376/306; 376/255
[58] Field of Search ............................ 204/404, 153.11; 376/245, 305, 301, 306, 255

[56] References Cited

U.S. PATENT DOCUMENTS

| | | | |
|---|---|---|---|
| 4,937,038 | 6/1990 | Sakai ........................ | 376/245 |
| 5,135,709 | 8/1992 | Andresen et al. ........... | 376/305 |
| 5,185,798 | 2/1993 | Sakai et al. ................. | 204/153.1 |
| 5,203,984 | 4/1993 | Sakai et al. ................. | 204/435 |
| 5,398,262 | 3/1995 | Ibe et al. .................... | 376/305 |
| 5,435,969 | 7/1995 | Hoots et al. ................. | 422/14 |
| 5,437,773 | 8/1995 | Glass et al. ................. | 204/153.11 |

FOREIGN PATENT DOCUMENTS 5-100087(A)   4/1993   Japan .

OTHER PUBLICATIONS

Rohn 2-page brochure, "Fiberglass Poles", copyright 1993.
Rohn 4-page brochure, "ROHN Steel Poles", copyright 1993.
Rohn 4-page brochure, "ROHN Concrete Poles", copyright 1994.
'Viability of Hydrogen Water Chemistry for Protecting In-Vessel Components of Boiling Water Reactors' by D. D. Macdonald, "Corrosion" Published on Mar. 1992, by National association of Corrosion Engineers.
'Electrochemical Potential Measurement Under Simulated BWR Water Chemistry Conditions' by C. C. Lin, F. R. Smith, N. Ichikawa, and M. Itow, "Corrosion" published on Jan. 1992, by Nation association of Corrosion Engineers.
'Corrosion Potential Measurements on Type 304 SS and Alloy 182 in Simulated BWR Environments' by D. D. Macdonald, H. Song, K. Makela, and K. Yoshida, "Corrosion" published on Jan. 1993, by National association of Corrosion Engineers.
'Use of Rotating Cylinder Electrodes to Simulate Turbulent Flow Conditions in Corroding Systems' by R. A. Holser, G. Prentice R. B. Pond Jr., and R. Guanti "Corrosion" published on Sep. 1990, by National association of Corrosion Engineers.

Primary Examiner—Charles T. Jordan
Assistant Examiner—Meena Chelliah
Attorney, Agent, or Firm—Pennie & Edmonds

[57] ABSTRACT

A system for monitoring the operation of a plant, which includes the facility of simulating the corrosion potential of a material and which can assess the effect of a countermeasure for mitigating the corrosion environment of the material, with the corrosion potential obtained by the simulation. The corrosion potential of the structural material of the plant is computed through a numerical analysis by applying an electrochemical mixed-potential theorem on the basis of the analytical result of a charge transfer reaction. Programs for such potential computations are prestored in a computer system from which data are accepted into a host computer. The computed corrosion potential is related with water quality data (for example, the concentration of hydrogen injected into the plant), and the relationship is output to a display unit.

14 Claims, 12 Drawing Sheets

F I G. 1
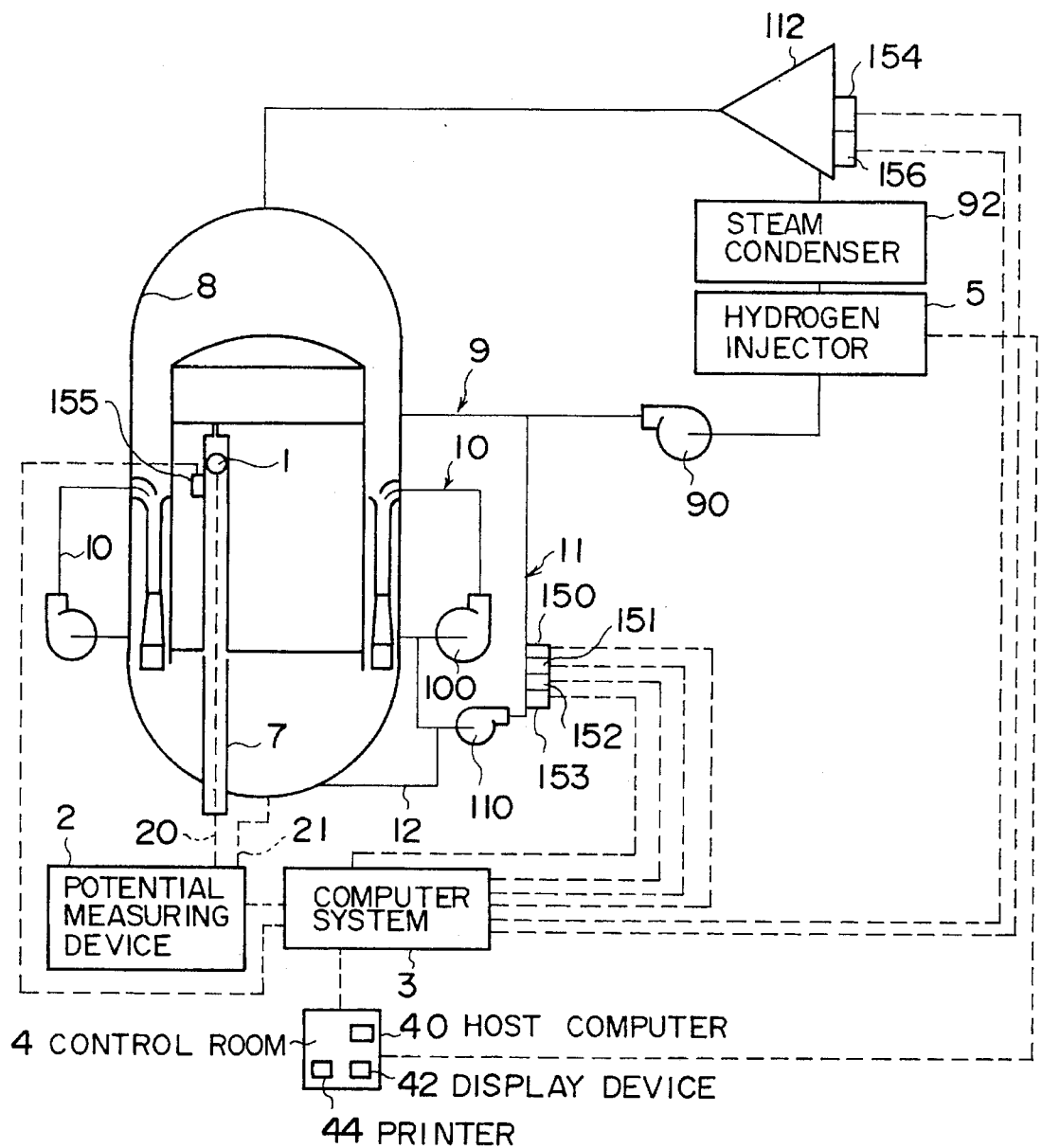

F I G. 11
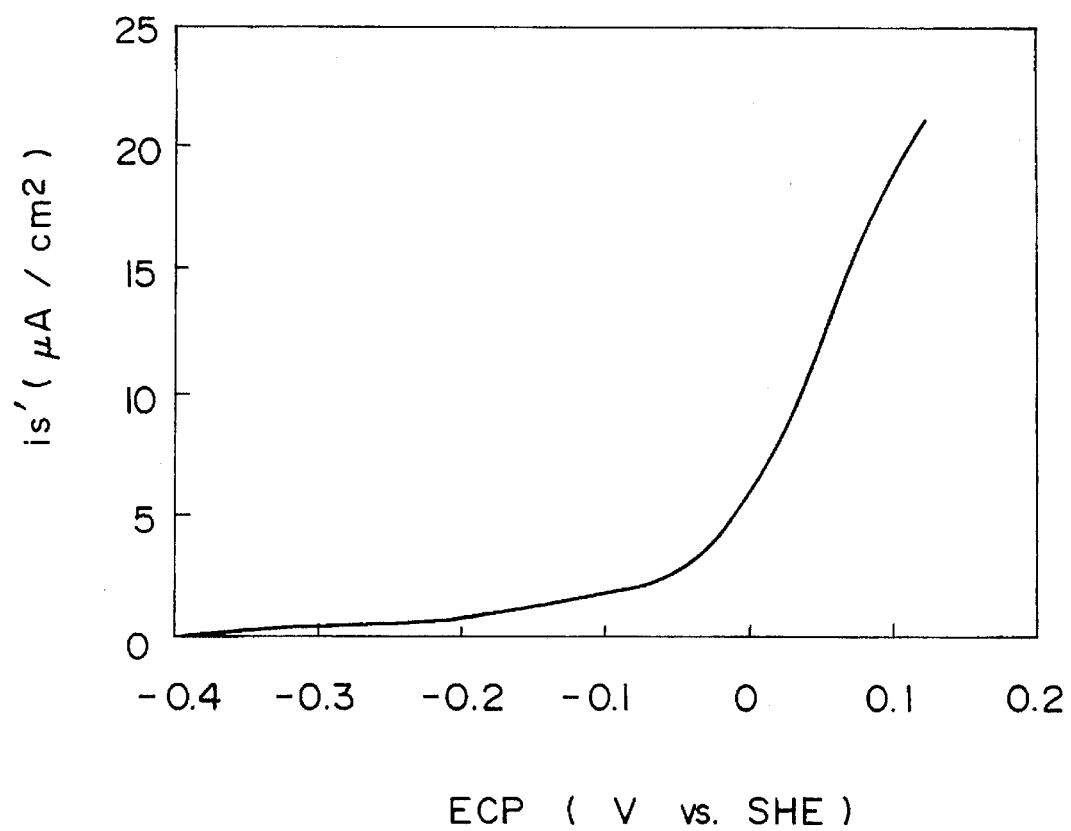

METHOD OF MEASURING A CORROSION POTENTIAL, METHOD OF SIMULATING POTENTIAL CHARACTERISTICS OF A REACTION RATE, AND PLANT MONITORING SYSTEM ADOPTING THEM

BACKGROUND OF THE INVENTION

1. Field of the Invention

The present invention relates to a system for monitoring a plant. More particularly, it relates to a plant operation monitoring system in which a corrosion potential being one of parameters indicative of a corrosion environment in a nuclear power plant or the like can be measured by utilizing a theoretical computation, and in which the effect of improving the water quality or chemistry of the plant can be studied using the measured result.

2. Description of the Related Art

In a nuclear power plant, oxygen, hydrogen peroxide, etc., which are the radiolytic products of reactor water, exist in the reactor water. A redox system which is constituted by the oxygen, hydrogen peroxide, etc., exhibits a high redox potential. On the other hand, a metallic structural material such as stainless steel, and hydrogen being the radiolytic product of water exhibit low potentials. These facts lead to the problem that the metallic structural material such as stainless steel is corroded (in general, as a corrosion potential is higher, a metal lies in an intenser oxidizing environment). At present, therefore, damage to structural materials in a nuclear reactor attributed to the above corrosion, stress corrosion cracking, etc. is suppressed by performing hydrogen injection. Herein, the hydrogen injection is a technique wherein hydrogen is injected into the reactor water of the nuclear reactor and is reacted with oxidants (such as oxygen, hydrogen peroxide, and intermediate radicals) contained in the reactor water, thereby lowering the concentrations of the oxidants and mitigating a corrosion environment in the reactor.

Meanwhile, the extent of the propagation of such corrosion has a close relation with the corrosion potential. The stress corrosion cracking, for example, has its threshold value at a corrosion potential of about −200 (mV) with reference to a standard hydrogen electrode (SHE). Accordingly, the measurement of the corrosion potential is indispensable for determining the conditions of the hydrogen injection.

In present-day plants, however, places where corrosion potential sensors can be mounted are limited, and the corrosion potentials cannot be measured at all objective parts to-be-monitored. It is therefore required to theoretically simulate the corrosion potential.

Besides, in order to predict and assess the effect of improvements in the water quality or chemistry of the plant owing to the hydrogen injection or the like, the corrosion potential needs to be analyzed in association with the actual chemical components etc. of the reactor water. A technique for theoretically simulating the corrosion potential is also required for this purpose.

Such potential simulations themselves have heretofore been conducted.

By way of example, Japanese Patent Application Laid-open No. 100087/1993 indicates a logical flow chart for a corrosion potential computation in a nuclear power plant system, and the basic reaction rate equation of a single charge-transfer reaction based on the fundamental charge-transfer reaction rate theorem (hereinbelow, this technique shall be called the "prior-art technique A").

Besides, a method of conjecturing a corrosion potential by a computation is stated in proceedings "Corrosion", 48, 3 (1992), pp. 194–205. The effect of the mitigation of the corrosion environment of a nuclear power plant system is also discussed (hereinbelow, called the "prior-art technique B").

A discussion on a corrosion potential is similarly contained in the proceedings "Corrosion", 48, 1 (1992), pp. 16–28 (hereinbelow, called the "prior-art technique C").

In the proceedings "Corrosion", 49, 1 (1993) pp. 8–16, corrosion potentials under the water quality environment of a nuclear power plant system are discussed, and the computed results of the potentials are also introduced (hereinbelow, called the "prior-art technique D").

Incidentally, a corrosion potential which is indicated by an electrochemical mixed-potentials theorem is obtained fundamentally by solving an equation ia−ic=0 to find a potential at which ia=ic holds. Here, "ic" denotes the reaction rate of a reaction system which accepts an electron, while "ia" denotes the reaction rate of a side which releases an electron (a side which is corroded).

According to the electrochemical mixed-potential theorem, the "corrosion potential" is construed to be a "mixed potential" in the state (dynamic equilibrium state) in which the respective reaction rates of the oxidizing reaction of an electron acceptor and the reducing reaction of an electron donor are equal in a certain redox system in which the corrosion reaction of a metal develops (it is to be noted that, in a case where the metal is relevant to the side of lower potential, the mixed potential of the redox system is usually called the "corrosion potential").

The "mixed potential" is determined by the rate at which the redox reaction of higher redox potential (equilibrium potential) accepts electrons from the redox reaction system of lower redox potential, and the rate at which the redox reaction system of the lower redox potential releases electrons.

The equilibrium potential of the redox reaction in each single system can be theoretically obtained through thermodynamical handling represented by the Nernst equation. In a system of two or more coexistent redox reactions, however, the equilibrium potential of the system can no longer be obtained any longer by simply applying the Nernst equation.

The reaction rate of each redox reaction cannot be found from only an overall reaction equation, but it can be determined for the first time by acquiring information down to the rate determining steps of the elementary reaction processes of each reaction. In simulating the corrosion potential of the actual corrosion reaction, accordingly, it becomes important that the rates of the charge transfer reactions relevant to the corrosion reaction are exactly expressed by formulae. Moreover, it is indispensable that the elementary processes determining the reaction rate, such as the rate determining steps of the actual reaction, are theoretically handled in rate theorem fashion.

Nevertheless, any of the logical flow chart or computational contents of the corrosion potential computations stated in the prior-art techniques is utilized in connection with the charge-transfer reaction rate equation concerning the single charge-transfer reaction. By way of example, the computation stated in the prior-art technique B is not based on charge-transfer reaction rate theory, but it is empirical handling. More specifically, notwithstanding that the simulation pertains to the multiple charge-transfer reaction, it handles the reaction rate equation in the single reaction. Accordingly, this technique B is still problematic in theory for the corrosion potential computation which requires the simulation based on a reaction mechanism. Besides, the prior-art technique C mentions nothing about the corrosion potential simulation which is based on the handling based on the charge-transfer reaction rate theory.

In other words, it is difficult to say that any of the prior-art techniques obtains the charge-transfer reaction rates of oxygen, hydrogen peroxide, hydrogen etc. using the handling based on the charge-transfer reaction mechanism. This point will now be explained in more detail.

The overall reaction of the reducing reaction of oxygen is indicated by Chemical formula 1:

$$O_2 + 4H^+ + 4e \rightarrow 2H_2O \qquad \text{[Chemical formula 1]}$$

Since it is difficult for this four-electron reaction to proceed in one step, the charge-transfer reaction mechanism thereof is a consecutive one in which hydrogen peroxide intervenes as an intermediate as indicated by Chemical formula 2:

$$O_2 + 2H^+ + 2e \rightleftharpoons H_2O_2 + 2H^+ + 2e \rightleftharpoons 2H_2O \qquad \text{[Chemical formula 2]}$$

Part of the hydrogen peroxide formed as the intermediate in Chemical formula 2 is decomposed in a bulk solution or at the surface of a material to revert to oxygen in accordance with the reaction of Chemical formula 3:

$$H_2O_2 \rightarrow \tfrac{1}{2} O_2 + H_2O \qquad \text{[Chemical formula 3]}$$

The oxygen formed by this decomposition accepts electrons from the structural material again, and is reduced to water by Chemical formula 2.

The above reactions cannot be handled independently, but the individual reaction processes thereof relate closely to one another.

In spite of this fact, the prior art handles the reactions under the assumption that the rates of the charge-transfer reactions of oxygen, hydrogen peroxide etc. do not affect one another. That is, the aforementioned chemical formula 2 is divided into the steps of the following chemical formulae 4 and 5 so as to obtain the charge-transfer reaction rates which correspond to the respective concentrations of oxygen and hydrogen peroxide:

$$O_2 + 2H^+ + 2e \rightarrow H_2O_2 \qquad \text{[Chemical formula 4]}$$

$$H_2O_2 + 2H^+ + 2e \rightarrow 2H_2O \qquad \text{[Chemical formula 5]}$$

It is considered that the reactants of hydrogen peroxide contained in Chemical formulae 4 and 5 will be indiscriminate and will act on both the reactions equally. The chemical formulae 4 and 5 cannot be independent of each other, and the reducing reaction of oxygen needs to be handled as the consecutive charge-transfer reaction mechanism given by Chemical formula 2. More specifically, the chemical formula 2 containing hydrogen peroxide as the intermediate consists in the complicated charge-transfer reaction mechanism of both forward and backward reactions. Herein, part of the hydrogen peroxide being the intermediate is decomposed into oxygen, which participates in the reactions of Chemical formula 2 again. Further, the concentration of the oxygen to be formed by the decomposition of the hydrogen peroxide is affected by both the forward and backward reaction rates of each charge-transfer reaction step of Chemical formula 2. It is accordingly impossible to handle the charge-transfer reactions of oxygen and hydrogen peroxide independently.

As thus far explained, neither the charge-transfer reaction rate equation based on the analysis at the elementary reaction level, nor the information items on the rate determining steps of the charge-transfer reactions are used in any of the potential simulations having hitherto been conducted. It can be said, at least, that any of the potential simulations is studied in accordance with a model which is different from the real phenomenon. In addition, the empirical formula is one mere expedient for elucidating an experimental result as to only a specified occasion and specified conditions. Since the empirical formula does not handle parameters admitted extensively and generally, it is often utterly inapplicable to a different environmental situation.

In the nuclear power plant, there coexist a plurality of sorts of electrochemical reaction systems which involve oxygen, hydrogen peroxide, hydrogen, metallic structural materials such as stainless steel, and so forth. There has not heretofore been any example in which the net charge-transfer reaction rates of the whole reaction system having the plurality of sorts of coexistent electrochemical reaction systems in this manner are analyzed and computed from elementary reaction models.

SUMMARY OF THE INVENTION

The present invention has for its object to provide a method in which a corrosion potential relating closely to the corrosion rate of a structural material or the like is theoretically obtained on the basis of an electrochemical mixed-potential theorem and a charge-transfer reaction rate theory. In particular, it has for its object to generalize and provide a technique in which the elementary-reaction analysis of a corrosion reaction is performed at a multistep charge-transfer reaction level, whereby the corrosion potential is handled theoretically at a higher accuracy.

Also, the present invention has for its object to provide a system for monitoring the operation of a plant with importance attached to an actual nuclear power plant, in which the corrosion potential of the structural material of the plant is theoretically simulated, thereby assisting in the preventive maintenance of the structural material of the plant and the water quality control of the plant.

In solving the problems of the prior art stated before, it is necessary to discuss the reaction rate theory at the level of the elementary-reaction analysis as forms the basis of the simulation. To this end, it is necessary to propose reaction models. The present invention has been made including such viewpoints.

In the first aspect of the present invention which has been made in order to accomplish the above objects, there is provided a plant monitoring system for monitoring a plant having a sensor which detects a concentration of at least one species of a certain specified substance existing within the plant; comprising a memory unit which stores therein a computational formula that is derived on the basis of a reaction rate equation relevant to a model of a reaction process including at least one step of electrochemical reaction, the specified substance participating in the electrochemical reaction within the plant, and information on a reaction rate of a reaction that is taking place as to a structural material of the plant; an arithmetic and control unit which computes a potential of the structural material by using the computational formula derived on the basis of the reaction rate equation, as well as the information on the reaction rate of the reaction taking place as to the structural material of the plant, the computational formula as well as the information being held stored in the memory unit, and the concentration of the specified substance detected by the sensor; and an output unit which delivers the potential of the structural material computed by the arithmetic and control unit.

In this case, the plant monitoring system may well be so constructed that the arithmetic and control unit further includes a facility of computing an environmental index indicative of a state of a certain specified environmental factor within the plant, on the basis of the concentration of the specified substance used in computing the potential of the structural material, and that the output unit further delivers the environmental index. Moreover, the output unit should preferably deliver the potential of the structural material and the environmental index as have been computed by the arithmetic and control unit, in an output pattern which indicates a corresponding relationship between them. Herein, the output unit may well deliver the potential of the structural material and the environmental index in the form of a graph whose axes respectively represent them.

It is also allowed that the plant includes an operating device which performs a certain specified operation capable of exerting influence on the environmental index; and that the output unit delivers a manipulated variable of the specified operation and the potential of the structural material computed by the arithmetic and control unit, in an output pattern which indicates a corresponding relationship between them.

It is also allowed that the plant is a nuclear power plant in which a reactor is cooled with reactor water, and it includes sensing means for detecting a state thereof; that the sensing means is constructed including at least one member selected from the group consisting of a potential sensor which detects the potential of the structural material of the plant; a dissolved oxygen sensor which detects the concentration of dissolved oxygen contained in the reactor water; a hydrogen peroxide sensor which detects the concentration of hydrogen peroxide contained in the reactor water; a pH sensor which detects the pH of the reactor water; an electric conductivity sensor which detects an electric conductivity of the reactor water; a potential sensor which detects a potential of an inactive metal contained in the reactor water; a radioactive nitrogen sensor which detects radioactive nitrogen contained in steam generated by vaporization of the reactor water; a crack propagation rate sensor which detects a crack propagation situation of the structural material of the plant; and a radiation dose rate sensor which detects a radiation dose rate in the steam generated by the vaporization of the reactor water; and that the output unit delivers at least one of the detected results of the sensing means, together with the potential of the structural material computed by the arithmetic and control unit.

The specified substances may well be oxygen, hydrogen peroxide and hydrogen.

The information on the reaction rate of the reaction which might be taking place as to the structural material of the plant may well be information which indicates a current-potential relationship concerning the reaction.

The environmental index may well indicate a concentration of an oxidant within the plant.

The certain specified operation may well be injection of hydrogen.

The reaction process model may well contain hydrogen peroxide as an intermediate.

The reaction process may well include a reaction in which hydrogen peroxide is decomposed and/or formed in accordance with at least two steps of consecutive elementary electrochemical reaction processes and the chemical reaction process model.

It is also allowed that measured data which indicate a relationship between a propagation rate of stress corrosion cracking of the structural material of the plant and the potential of the structural material are prepared beforehand; that the arithmetic and control unit includes a facility of computing a corresponding relationship between the propagation rate of the stress corrosion cracking and the environmental index, by using the measured data and a corresponding relationship between the computed potential of the structural material and the environmental index; and that the output unit delivers the propagation rate of the stress corrosion cracking sand the environmental index, in an output pattern which indicates the corresponding relationship between them.

In the second aspect of the present invention, there is provided a plant monitoring system for monitoring a plant; comprising a sensor which detects a concentration of at least one species of certain specified substance existing within the plant; a memory unit which stores therein a computational formula that is derived on the basis of a reaction rate equation relevant to a model of a reaction process including at least one step of electrochemical reaction, the specified substance participating in the electrochemical reaction that is taking place within the plant, and information on a reaction rate of a reaction that is taking place as to a structural material of the plant; an arithmetic and control unit which computes a potential of the structural material by using the reaction rate equation and the information on the reaction rate as are stored in the memory unit, and the concentration of the specified substance detected by the sensor; and an output unit which delivers the potential of the structural material computed by the arithmetic and control unit.

In the third aspect of the present invention, there is provided a plant system comprising a vessel in which any reaction is conducted; a sensor which detects a concentration of at least one species of certain specified substance existing under an environment within the vessel; a memory unit which stores therein a formula reflective of a reaction rate equation that is derived in accordance with a model of at least one step of a reaction process, the specified substance seeming to participate in occurrence of the reaction process under the environment, and information on a reaction rate of a reaction that might be taking place as to a structural material of the vessel; an arithmetic and control unit which computes a potential of the structural material by using the formula reflective of the reaction rate equation and the information on the reaction rate as are stored in the memory unit, and the concentration of the specified substance detected by the sensor; and an output unit which delivers the potential of the structural material computed by the arithmetic and control unit.

In the fourth aspect of the present invention, there is provided a method of simulating potential characteristics of a reaction rate of a reaction process which includes an electrochemical reaction taking place in a certain material; comprising measuring a concentration of a substance which participates in the reaction process under a certain state, and a potential of the material; and obtaining a relationship between the reaction rate of the reaction process and the potential of the material by substituting the measured concentration of the substance and the measured potential of the material into a formula reflective of a reaction rate equation that is derived in accordance with a model of the reaction process.

Herein, the reaction rate should preferably be expressed as current values.

The reaction process should preferably include the following reactions (a) thru (e):

(a) $O_2 + 2H^+ + 2e \rightarrow H_2O_2$ (b) $H_2O_2 \rightarrow O_2 + 2H^+ + 2e$ (c) $H_2O_2 + 2H^+ + 2e \rightarrow 2H_2O$ (d) $H_2O_2 \rightarrow (\frac{1}{2})O_2 + H_2O$ (decomposition in bulk solution), and (e) $H_2O_2 \rightarrow (\frac{1}{2})O_2 + H_2O$ (surface catalytic decomposition)

In the fifth aspect of the present invention, there is provided a method of measuring a corrosion potential of a structural material of a plant, comprising computing a potential at which reaction rates of an anode reaction and a cathode reaction included in a corrosion reaction become equal, through a numerical analysis on the basis of an electrochemical mixed potential theorem by using a computational formula that is derived from a reaction rate, equation relevant to a reaction model of the corrosion reaction indicated by at least one step of reaction process; reaction rate information on the corrosion reaction of the structural material; and a concentration of a substance that participates in the corrosion reaction; the computed potential being determined as the corrosion potential.

In the measurement method, in a case where the plant is a nuclear power plant, one of the reaction rate equations concerning the reaction process should preferably be an equation of a charge transfer reaction rate including concentrations of oxygen and hydrogen peroxide at a surface of the material.

Also, in a case where the plant is a nuclear power plant, one of the reaction rate equations concerning the reaction process should preferably be an equation of a charge transfer reaction rate including a concentration of hydrogen at a surface of the material, a concentration of protons at the surface of the material, and a concentration of atomic-state hydrogen adsorbed by the material.

Herein, the material may well be a member selected from the group consisting of a pure metal and an alloy.

Besides, the alloy may well be a member selected from the group consisting of stainless steel, a nickel-based alloy, and carbon steel.

The operations of the first, second and third aspects will now be explained.

The arithmetic and control unit computes the potential of the structural material of the plant by using the computational formula derived on the basis of the reaction rate equation, as well as the information on the reaction rate of the reaction taking place as to the structural material, the computational formula as well as the information being held stored in the memory unit, and the concentration of the specified substance detected by the sensor. The output unit delivers the computed potential of the structural material.

The concrete contents of the method of computing the corrosion potential are as stated below.

Each of the redox reactions in the reactor water and at the surface of the material is defined as the reaction models of the charge-transfer reaction processes which proceed with one or more steps, and the theoretical overall charge-transfer reaction rates are obtained as to these reaction models. Both the oxidizing reaction and the reducing reaction are handled in this manner. Subsequently, the equation based on the electrochemical mixed-potential theory (that is, ia−ic=0 mentioned before) is solved for the potential by substituting the obtained reaction rates thereinto. Thus, the corrosion potential can be found by the computation. By the way, in a case where the modeling of the reactions is difficult, a regression equation based on the measured data may be obtained and then applied to the mixed-potential theory. Besides, the arithmetic and control unit computes the environmental index (for example, the oxidant concentration) on the basis of the concentration of the specified substance. The output unit delivers the environmental index in the output pattern which indicates the corresponding relationship thereof with the computed potential (as, for example, the graph whose axes respectively represent the potential of the structural material and the environmental index).

Further, the output unit delivers the manipulated variable of the specified operation (for example, the hydrogen injection) and the potential of the structural material computed by the arithmetic and control unit, in the output pattern which indicates the corresponding relationship between them.

In the case where the plant is the nuclear power plant in which the reactor is cooled with the reactor water, the output unit simultaneously delivers at least one of the corrosion potential, the concentration of the dissolved oxygen contained in the reactor water, the concentration of the hydrogen peroxide contained in the reactor water, the pH of the reactor water, the electrical conductivity of the reactor water, the potential of the inactive metal contained in the reactor water, the radioactive nitrogen contained in the steam generated by the vaporization of the reactor water, the crack propagation situation of the structural material, and the radiation dose rate in the steam. Thus, ascertaining the operating state of the plant is facilitated.

Moreover, the arithmetic and control unit computes the corresponding relationship between the propagation rate of the stress corrosion cracking and the environmental index, by using the measured data and the corresponding relationship between the computed potential of the structural material and the environmental index. The output unit delivers the propagation rate of the stress corrosion cracking and the environmental index, in the output pattern which indicates the corresponding relationship between them.

The operation of the fourth aspect of the present invention will now be explained.

The concentration of the substance participating in the reaction, in the certain state (for example, the equilibrium state) of the reaction process, and the measured value of the potential of the material in this state, are substituted into the reaction rate equation which is derived in accordance with the reaction process model. Thus, the relationship between the reaction rate (the current values) and the potential of the material can be obtained.

The operation of the fifth aspect of the present invention will now be explained.

The potential at which the reaction rates of the anode reaction and the cathode reaction included in the corrosion reaction become equal, is computed through the numerical analysis on the basis of the electrochemical mixed-potential theorem by using the reaction rate equation that is derived in accordance with the reaction model of the corrosion reaction indicated by at least one step of reaction process; the reaction rate information on the corrosion reaction of the structural material; and the concentration of the substance that participates in the corrosion reaction.

BRIEF DESCRIPTION OF THE DRAWINGS

FIG. 1 is a diagram showing the outlines of a nuclear reactor, and a reactor operation state monitoring system which is an embodiment of the present invention;

FIG. 11 is a graph showing the current-potential curve of stainless steel obtained through a computation by using the measured data of a corrosion potential;

PREFERRED EMBODIMENTS OF THE INVENTION

Figure 2:
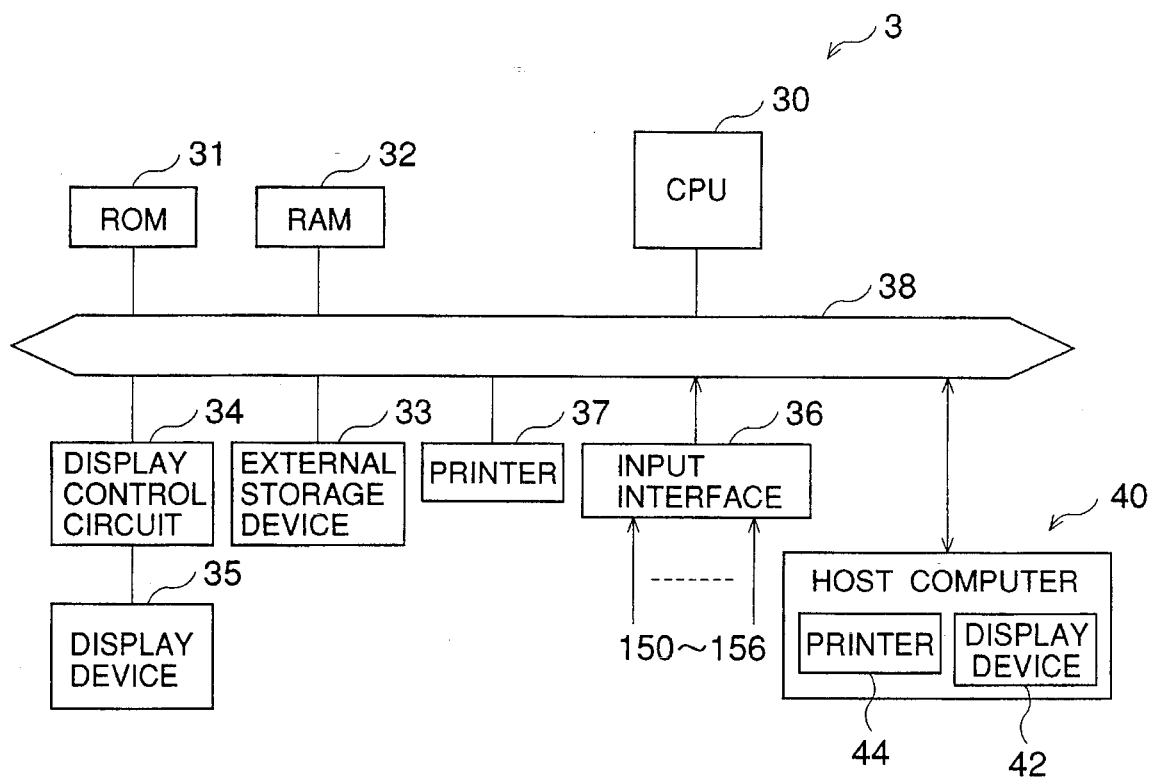
FIG. 2 is a block diagram showing the hardware architecture of a computer system (3) in the embodiment.

A plant monitoring system which is an embodiment of the present invention, will be described with reference to the drawings.

The plant monitoring system of this embodiment, and the plant itself of a nuclear reactor to which this embodiment is to be applied, will be briefly explained with reference to FIG. 1.

The plant of the nuclear reactor (of, for example, light-water type) is constructed including a reactor pressure vessel 8 for reacting fuel therein, a feed water system 9, a recirculation system 10 for reactor water, and a cleanup system (treatment system) 11 for the reactor water. Incidentally, the reactor pressure vessel 8 to which this embodiment is directed is made of stainless steel (SUS304-group in JIS).

The feed water system 9 cools steam resulting from the heating of the reactor water within the reactor pressure vessel 8, and returns the recovered reactor water into the reactor pressure vessel 8 again. Arranged in sequence before the feed water system 9 are a turbine system 112 for power generation, a steam condenser 92, and a hydrogen injector 5. Electric power is generated by actuating the turbine system 112 with the steam. The steam having rotated the turbine of the turbine system 112 is recovered into the liquid by the steam condenser 92.

The hydrogen injector 5 serves to mitigate a corrosion environment in the nuclear power plant by injecting hydrogen into the reactor water. This hydrogen injector 5 injects the hydrogen into the feed water system 9 so as to establish a predetermined hydrogen concentration, in accordance with an instruction sent thereto from a control room 4 to be explained later. The amount of injection of the hydrogen is determined as sufficient values necessary for preventing stress corrosion cracking etc., by the use of the simulation results of a computer system 3, etc. as will be explained later. Incidentally, the relationship between the actual hydrogen concentration in the feed water system 9 and the injection amount of the hydrogen is measured beforehand. The instruction for the hydrogen injector 5 is given in such a form as "SET HYDROGEN CONCENTRATION AT 15 (ppb)" by way of example.

The reactor water recirculation system 10 serves to render a temperature distribution in the reactor pressure vessel 8 and the corrosion environment (for example, the oxidant concentration of the reactor water) homogeneous by circulating the reactor water within the reactor pressure vessel 8.

The reactor water cleanup system 11 serves to clean up the reactor water of the nuclear reactor. This reactor water cleanup system 11 takes in the reactor water from the intermediate part of the reactor water recirculation system 10, and cleans it up. Thereafter, it returns the reactor water into the reactor pressure vessel 8 through the feed water system 9. The reactor water lying in the bottom of the pressure vessel 8 is also flowing into the reactor water cleanup system 11 through a bottom drain line 12.

By the way, the feed water system 9, reactor water recirculation system 10 and reactor water cleanup system 11 are respectively furnished with pumps 90, 100 and 110.

Mounted on the reactor pressure vessel 8, feed water system 9, reactor water recirculation system 10 and reactor water cleanup system 11 are various sensors and measuring devices for detecting the situations of the reactor water and structural materials constituting these components.

A reference electrode 1 and a potential measuring device 2 serve to measure a corrosion potential at the certain specified objective part to-be-measured of the structural member which is included in the reactor pressure vessel 8.

The reference electrode 1 serves to generate a potential which is used as the reference of the potential measurement. A platinum electrode is employed as the reference electrode 1 in this embodiment, but it may well be replaced with a silver/silver chloride electrode. Besides, the reference electrode 1 is attached to a neutron instrumentation pipe 7 in this embodiment.

The potential measuring device 2 serves to find the potential of the objective part to-be-measured with reference to the potential of the reference electrode 1. This potential measuring device 2 is furnished as its input lines with a potential signal cable 20 which is extended from the reference electrode 1, and a potential signal cable 21 which is connected to the reactor pressure vessel 8 electrically short-circuited with the structural material of the nuclear reactor. In this embodiment, the potential of the objective part is measured versus the standard hydrogen electrode (SHE). Needless to say, the potential measuring device 2 to be used is one having a sufficiently high input impedance.

Further, the reactor pressure vessel 8 and the reactor water cleanup system 11 are furnished with a dissolved-oxygen sensor 150, a hydrogen peroxide sensor 151, a pH sensor 152, an electrical-conductivity sensor 153, a sensor 154 for radioactive nitrogen contained in the main steam, a crack propagation rate sensor 155, and a sensor 156 for the radiation dose rate of the main steam system 12. As these sensors, various types have been put into practical use or have been proposed, and any of them may be employed in this embodiment. Moreover, the mounting positions of these sensors are not restricted to those indicated in FIG. 1.

The computer system 3 serves to process the detected results of the various sensors including the potential measuring device 2. As illustrated in FIG. 2, the computer system 3 itself is chiefly configured of hardware resources such as a processor (CPU) 30, a ROM 31, a RAM 32, an external memory 33, a display control circuit 34, a display unit 35, an input interface 36, a printer 37, and a bus 38 connecting these components, and programs which are stored in the external memory 33, RAM 32 and ROM 31 and which are run by the processor 30. Herein, the processed results of the processor 30 are delivered to the display unit 35 through the display control circuit 34 or to the printer 37 in the form of characters or graphics. Further, they are delivered to a host computer 40, a display unit 42, a printer 44, etc. which are installed in the control room 4.

One of the programs prestored in the external memory 33, RAM 32 and ROM 31 of the computer system 3 in this embodiment is for simulating the corrosion potential on the basis of the presumed water quality data of the objective part to-be-monitored, the water analysis data of sampled water, etc. The processor 30 of the computer system 3 has the facility of executing the simulation program, thereby obtaining information on the corrosion potential. Also, data etc. which are required for implementing various facilities to be detailed later are stored in the external memory 33, etc. beforehand. In addition, the processor 30 causes the display unit 35 to display the processed results thereof through the display control circuit 34. Since such facilities are the most important features of this embodiment, they shall be described in detail later. Further, the computer system 3 includes the program for computing an oxidant concentration ($O_2^*$) in the nuclear reactor on the basis of the dissolved oxygen concentration of the reactor water.

The control room 4 is a room where the operator of the nuclear power plant actually monitors the operation thereof. Arranged in the control room 4 are the host computer 40 which accepts data from the computer system 3, the display unit 42, the printer 44, and various control devices. The display unit 42, etc. are adapted to indicate the corrosion-potential computation result of the computer system 3, along with various measurement data (for example, in-situ data, water-quality analysis data and corrosion-potential measurement data), preset data reference values, etc. The operator can monitor the operating state of the nuclear reactor by watching the indications. Subject to some indicated results, he/she performs, for example, the alterations of the operating situations of the nuclear reactor by manipulating the control devices.

Next, the details of the corrosion potential computation by the computer system 3 in this embodiment will be described.

Figure 3:
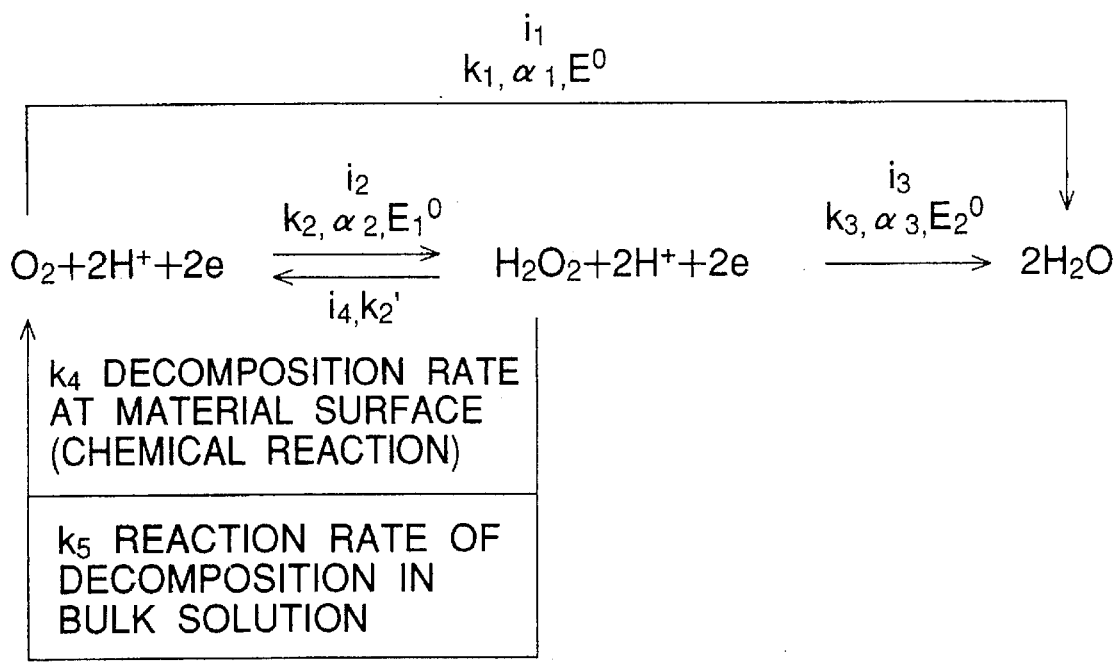
FIG. 3 shows an elementary chemical charge-transfer reaction model of multiple steps for oxygen and hydrogen peroxide which are contained in the light-water nuclear reactor.

The corrosion potential of the objective part to-be-measured is obtained by solving Equation 1 given below, with respect to a potential. More specifically, Equation 1 is defined as an equation which contains the corrosion potential, an oxygen concentration, a hydrogen peroxide concentration, a hydrogen concentration and a flow velocity as variables, in the following way: Computational formulae, which are derived from reaction rate equations concerning reaction models to be stated later (elementary chemical charge-transfer reaction models for oxygen and hydrogen peroxide and for hydrogen as shown in FIG. 3 and in FIG. 4, respectively), are respectively substituted into terms "i" and "ih" among three terms ("i", "ih" and "is") included in Equation 1, while a formula, which is obtained by formulating a measured current-potential curve (the 9th-order least-squared approximation curve of a current-potential curve for stainless steel as shown in FIG. 5), is substituted into the term "is". Subsequently, the equation defined in this way is given the oxygen concentration, hydrogen peroxide concentration, hydrogen concentration and flow velocity as input data, whereby it can be transformed into an equation which contains only the corrosion potential as a variable. Finally, the equation containing only the corrosion potential as a variable is solved, whereby the corrosion potential can be obtained.

The equation containing the five variables (corrosion potential, oxygen concentration, hydrogen peroxide concentration, hydrogen concentration and flow velocity) mentioned above is stored in the program of the computer system 3 of this embodiment beforehand. Four of the five variables, namely, the oxygen, hydrogen peroxide and hydrogen concentrations (in ppb) and the flow velocity (in cm/s) are afforded to the computer system 3 as the input data, and the obtained equation is solved, whereby the corrosion potential is computed. By the way, numerical analysis is only one method of solving the equation. In this embodiment, the equation is solved by the Newton method.

$$i - ih - is = 0 \qquad \text{[Equation 1]}$$

Here, letter "i" denotes in terms of an electric current, a rate at which an oxygen/hydrogen peroxide system in the reactor water accepts electrons at a certain corrosion potential value. The current "i" corresponds to a total current which is externally measured. Symbol "ih" denotes in terms of electrics current, a rate at which hydrogen in the reactor water releases an electron at the certain corrosion potential value. Symbol "is" denotes the electron releasing rate of stainless steel at the certain corrosion potential value in terms of an electric current. The details of Equation 1 come to reflect the contents of a corrosion reaction. Accordingly, how a reaction model is used becomes decisively important for enhancing the credibility of a calculated corrosion potential. Therefore, the reaction model assumed shall be also elucidated.

There will now be detailed the contents, theoretical formulae, theoretical formula deriving steps, etc. of the terms "i", "ih" and "is" employed in the potential computation.

First, the term "i" will be explained.

Those charge transfer reactions and chemical reactions of oxygen and hydrogen peroxide which are relevant to the corrosion reaction have been assumed to include processes indicated by Chemical formulae 6, 7, 8, 9 and 10 listed below. In the simulation, the individual processes indicated by Chemical formulae 6 to 10 have been handled as elementary reactions.

$O_2 + 2H^+ + 2e \rightarrow H_2O_2$ [Chemical formula 6]

$H_2O_2 \rightarrow O_2 + 2H^+ + 2e$ [Chemical formula 7]

$H_2O_2 + 2H^+ + 2e \rightarrow 2H_2O$ [Chemical formula 8]

$H_2O_2 \rightarrow (\frac{1}{2})O_2 + H_2O$ (Decomposition in bulk solution) [Chemical formula 9]

$H_2O_2 \rightarrow (\frac{1}{2})O_2 + H_2O$ (Surface catalytic decomposition) [Chemical formula 10]

It is FIG. 3 that illustrates the correlations of Chemical formulae 6 to 10. In the figure, some of the chemical formulae are omitted for simplification. Although the reverse reactions of Chemical formula 8, etc. might exist, such reverse reactions have not been considered in this embodiment.

In the above, Chemical formula 6 indicates a reducing reaction based on the consecutive electron transfers of oxygen, and the formation of hydrogen peroxide being the intermediate of the electrochemical reducing reaction of oxygen. Chemical formula 7 indicates the consumptive process of hydrogen peroxide being the intermediate of the electrochemical reducing reaction of oxygen, and the process of the electrochemical decomposing reaction of hydrogen peroxide. Chemical formula 8 indicates the consumptive process of hydrogen peroxide being the intermediate of the electrochemical reducing reaction of oxygen, and a reducing reaction based on the consecutive electron transfers of oxygen. Chemical formula 9 indicates a decomposing reaction in the diffusional process of hydrogen peroxide being the intermediate of the reducing reaction of oxygen. Chemical formula 10 indicates the process of the catalytic decomposition reaction of hydrogen peroxide at the surface of the structural material.

The rate of the overall reaction is expressed by the total current density "i" ($A/cm^2$). Since the five processes (Chemical formulae 6 to 10) listed here proceed at the same time, the total current density "i" is indicated by the following equation 2:

$$i = i_1 + i_2 + i_3 - i_4 \quad \text{[Equation 2]}$$

Terms $i_1$, $i_2$, $i_3$ and $i_4$ in Equation 2 correspond to $i_1$, $i_2$, $i_3$ and $i_4$ mentioned in FIG. 3, respectively. In Equation 2, each cathode reaction (which accepts electrons) is set as being positive.

Accordingly, the total current density "i" is expressed using the equation of the overall reaction rate, by the following equation 3:

$$i = 2F[(2k_1 + k_2)C_{As} + (k_3 - k_2')C_{Bs}] \quad \text{[Equation 3]}$$

Letter "F" in Equation 3 denotes the Faraday constant. Character expressions $k_1$, $k_2$, $k_3$ and $k_2'$ are respectively indicated by Equations 8, 9, 10 and 11 to be given later.

Equation 3 contains the surface concentration $C_{As}$ of oxygen, the surface concentration $C_{Bs}$ of hydrogen peroxide, and the potentials thereof. The respective surface concentrations $C_{As}$ and $C_{Bs}$ of oxygen and hydrogen peroxide cannot be actually measured. However, they can be respectively expressed as the formulae of the bulk concentration $C_A$ of oxygen in the reactor water and that $C_B$ of hydrogen peroxide by solving differential equations which concern the diffusions of oxygen and hydrogen peroxide.

A method for expressing the respective surface concentrations $C_{As}$ and $C_{Bs}$ of oxygen and hydrogen peroxide in terms of the bulk concentrations $C_A$ and $C_B$ will be elucidated below.

Assuming that the diffusions in the vicinity of the surface of the structural material are linear diffusions, the diffusion processes of oxygen and hydrogen peroxide are respectively indicated by Equations 4 and 5. In these equations, letter "x" denotes a distance taken from the surface of the structural material, and x=0 corresponds to the position of the surface of the structural material.

$$\partial C_A(x,t)/\partial t = D_A[\partial^2 C_A(x,t)/\partial x^2] + (k_5/2)C_B(x,t) \quad \text{[Equation 4]}$$

$$\partial C_B(x,t)/\partial t = D_B[\partial^2 C_B(x,t)/\partial x^2] - k_5 C_B(x,t) \quad \text{[Equation 5]}$$

Here, letter "A" denotes oxygen ($O_2$), letter "B" hydrogen peroxide ($H_2O_2$), symbol "Cj" the concentration ($mol/cm^3$) of chemical species "j", symbol "Dj" the diffusion coefficient ($cm^2/s$) of the chemical species "j", and symbol "$k_5$" the decomposition rate constant (l/s) of hydrogen peroxide in the diffusion process.

In addition, a mass or material balance (boundary conditions) at the surface of the structural material is expressed by Equations 6 and 7 given below. The details of the character expressions contained in Equations 6 and 7 are indicated by Equations 8, 9, 10 and 11.

$$D_A[\partial C_A(x,t)/\partial x]x=0 = (k_1 + k_2)C_{As} - (k_2' + k_4 2)C_{Bs} \quad \text{[Equation 6]}$$

$$D_B[\partial C_B(x,t)/\partial x]x=0 = (k_2' + k_3 + k_4)C_{Bs} - k_2 C_{As} \quad \text{[Equation 7]}$$

$$k_1 = k_1^o \exp\{-4\alpha_1 F(E-E^o)/RT\}[H^+]^4 \text{ (cm/s)} \quad \text{[Equation 8]}$$

$$k_2 = k_2^o \exp\{-2\alpha_2 F(E-E_1^o)/RT\}[H^{3O}]^2 \text{ (cm/s)} \quad \text{[Equation 9]}$$

$$k_2' = k_2^{o'} \exp\{2(1-\alpha_2)F(E-E_1^o)/RT\} \text{ (cm/s)} \quad \text{[Equation 10]}$$

$$k_3 = k_3^o \exp\{-2\alpha_3 F(E-E_2^o)/RT\}[H^+]^2 \text{cm/s)} \quad \text{[Equation 11]}$$

In the above equations, symbol "$k_4$" denotes the decomposition rate constant (cm/s) of hydrogen peroxide at the material surface. Symbols "$\alpha_1$", "$\alpha_2$" and "$\alpha_3$" denote transfer coefficients in the reduction directions of the respective reaction steps. A proton concentration poses no problem in handling as a constant which is determined by the equilibrium of water dissociation. Quantities "$k_1^o [H^+]^4$" (cm/s), "$k_2^o [H^+]^2$" (cm/s), "$k_2^{o'}$" (cm/s) and "$k_3^o [H^+]^2$" (cm/s) are constant terms which concern the rates of the respective reaction steps. Letter "E" denotes the potential (V) of the structural material versus the reference electrode. Symbols $E"E^o$", "$E_1^o$" and "$E_2^o$" denote the standard electrode potentials (V) of the respective reaction steps. Letters "F", "R" and "T" denote the Faraday constant, the gas constant (8.32) and the absolute temperature, respectively.

Considering that the corrosion potential is information of a steady-state level with respect to time, the equation of the overall reaction rate will be satisfactorily derived by handling in the steady state of the diffusions. Therefore, the following equations 12 to 16 can be adopted as the boundary conditions of the diffusions:

$$\partial C_A(x,t)/\partial t = \partial C_B(x,t)/\partial t = 0 \quad \text{[Equation 12]}$$

$$X \geq \partial_A; \ C_A(x) = C_{A*} \quad \text{[Equation 13]}$$

$$X \geq \partial_B; \ C_B(x) = C_{B*} \quad \text{[Equation 14]}$$

$$X = 0; \ C_A = C_{As} \quad \text{[Equation 15]}$$

$$X = 0; \ C_B = C_{Bs} \quad \text{[Equation 16]}$$

Here, symbol "$\delta j$" denotes the thickness (cm) of the diffusion layer of the chemical species "j", symbol "Cjs" the concentration ($mol/cm^3$) of the chemical species "j" at the material surface, and symbol "Cj*" the equilibrium bulk concentration ($mol/cm^3$) of the chemical species "j" in the reactor water.

The surface concentrations $C_{As}$ and $C_{Bs}$ of oxygen and hydrogen peroxide can be respectively written in terms of the bulk concentrations $C_A$ and $C_B$ thereof by solving the simultaneous equations of Equations 4 to 16 mentioned above.

The values $C_{As}$ and $C_{Bs}$ computed using Equations 4 to 16 are substituted into Equation 3, and the result obtained is expressed in a simplified form by the following equation 17:

$$i = 2F(\zeta_1 \Xi_1 + \zeta_2 \Xi_2) \quad \text{[Equation 17]}$$

The details of character expressions contained in Equation 17 are as indicated by Equations 18 to 28 below. Incidentally, "$\Xi_1$" and "$\Xi_2$" are terms each having the dimension of a concentration (refer to Equations 21 and 22). Symbol "$\zeta_3$" in Equation 20 denotes a character expression which is contained in Equations 21 and 22.

$$\zeta_1 = 2k_1 + k_2 \text{ (cm/s)} \quad \text{[Equation 18]}$$

$$\zeta_2 = k_3 - k_2' \text{ (cm/s)} \quad \text{[Equation 19]}$$

$$\zeta_3 = k_1 + k_2 + D_A/\delta_A \text{ (cm/s)} \quad \text{[Equation 20]}$$

$$\Xi_1 = (\Lambda_1 \phi_2 + \Lambda_2 \phi_1)/[\zeta_3 \phi_2 + \quad \text{[Equation 21]}$$

$$\phi_1 k_2^\circ \exp\{-(2\alpha_2 F/RT)(E - E_I^\circ)\}[H^+]^2] \text{ (mol/cm}^3\text{)}$$

$$\Xi_2 = [\zeta_3 \Lambda_2 - \Lambda_1 k_2^\circ \exp\{-(2\alpha_2 F/RT)(E - E_I^\circ)\} [H^+]^2]/ \quad \text{[Equation 22]}$$

$$[\zeta_3 \phi_2 + \phi_1 k_2^\circ \exp\{-(2\alpha_2 F/RT)(E - E_I^\circ)\}[H^+]^2] \text{ (mol/cm}^3\text{)}$$

The following equations 23 to 28 indicate the details of character expressions contained in Equations 18 to 22:

$$\Lambda_1 = C_A * D/\delta_A - (C_B * D_B/2\delta_A)\{exp(-\lambda_2) + exp(\lambda_2) + 2\lambda_2\}/\{exp(-\lambda_1) - exp(\lambda_1)\} \quad \text{[Equation 23]}$$

$$\Lambda_2 = 2D_B C_B * \sqrt{(k_5/D_B)}[1/\{exp(-\lambda_1) - exp(\lambda_1)\}] \quad \text{[Equation 24]}$$

$$\Phi_1 = (D_B/2\delta_A)[exp(-\lambda_1)\{exp(\lambda_2) - \lambda_2\} - \quad \text{[Equation 25]}$$

$$exp(\lambda_1)\{exp(-\lambda_2) + \lambda_2\}]/\{exp(-\lambda_1) - exp(\lambda_1)\} + k_2' + k_4/2 - D_B/2\delta_A$$

$$\Phi_2 = D_B \sqrt{(k_5/D_B)}\{exp(-\lambda_1) + exp(\lambda_1)\}/ \quad \text{[Equation 26]}$$

$$\{exp(-\lambda_1) - exp(\lambda_1)\} - k_2' - k_3 - k_4$$

$$\lambda_{1+sc} = \delta_B \sqrt{(k_5/D_B)} \quad \text{[Equation 27]}$$

$$\lambda_{2+sc} = \delta_A \sqrt{(k_5/D_B)} \quad \text{[Equation 28]}$$

In addition, symbol "$k_1$" contained in the above equations is as defined by Equation 8. Symbol "$k_2$" is as defined by Equation 9. Symbol "$k_2'$" is as defined by Equation 10. Symbol "$k_3$" is as defined by Equation 11.

Next, the quantity "ih" contained in Equation 1 will be elucidated.

It has been assumed that the charge transfer reaction and chemical reaction of hydrogen relevant to the corrosion reaction proceed including processes (elementary reactions) indicated by Chemical formulae 11 to 18 below. Here, the individual processes expressed by these chemical formulae have been respectively handled as the elementary reactions.

H−e→H....H  [Chemical formula 11]

H.....H⁺+e→H₂  [Chemical formula 12]

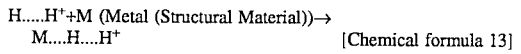
H.....H⁺+M (Metal (Structural Material))→
M....H....H⁺  [Chemical formula 13]

M...H...H⁺→H....H⁺+M  [Chemical formula 14]

M...H...H⁺−e→M+2H⁺  [Chemical formula 15]

M+2H⁺+e→M...H...H⁺  [Chemical formula 16]

H₂O→H⁺+OH⁻  [Chemical formula 17]

H⁺+OH⁻→H₂O  [Chemical formula 18]

Figure 4:
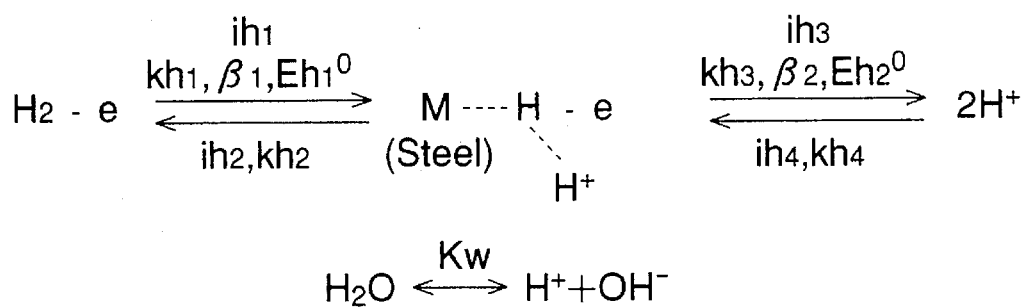
FIG. 4 shows a multistep elementary chemical charge-transfer reaction model for hydrogen which is contained in the light-water nuclear reactor.
Figure 5:
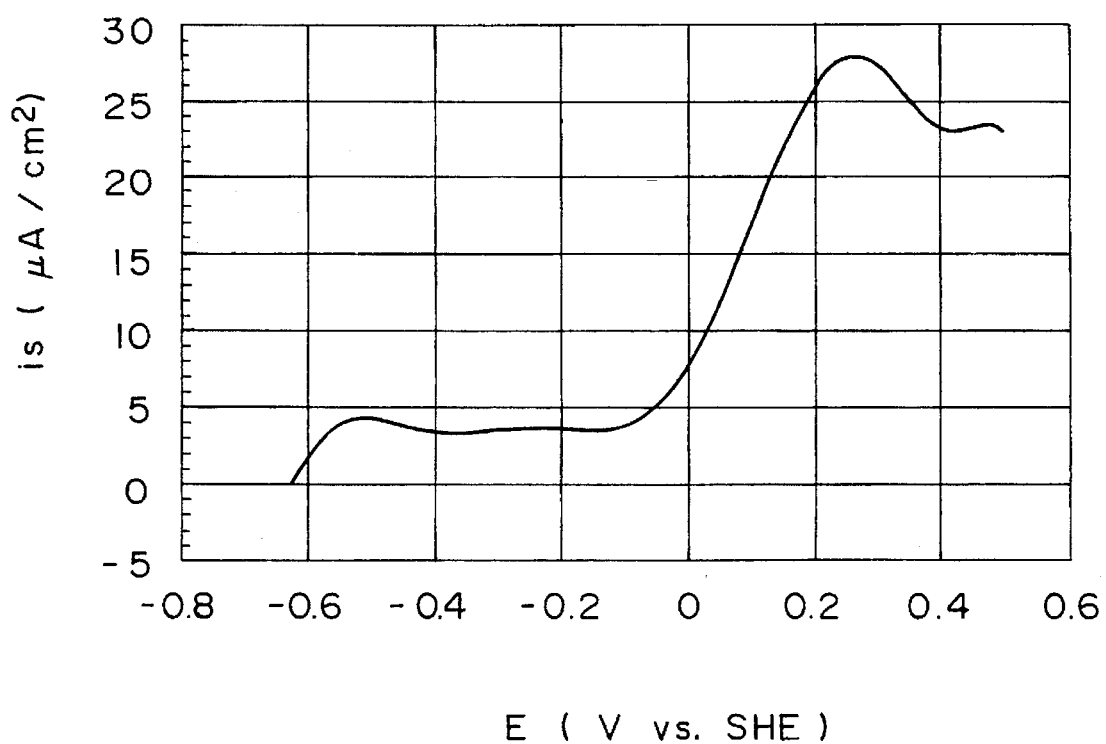
FIG. 5 shows the approximate curve of a current potential curve measured for stainless steel.

FIG. 4 illustrates the correlations of Chemical formulae 11 to 18.

These processes constitute a mechanism of consecutive single-electron reactions. Atomic-state hydrogen adsorbed by the structural material participates in the reactions as an intermediate. The equilibrium of the water dissociation reaction relates to the initial concentration of $H_3O^+$ ions at the surface of the structural material and the bulk concentration thereof in the reactor water. Incidentally, the equilibrium constant Kw of water dissociation is $Kw = 2.5 \times 10^{-12}$ (mol/l)². The rate of the reaction between $H_3O^+$ and $OH^-$ ions is the fastest as the reaction rate of the secondary reaction of a homogeneous system. Therefore, it poses no problem in handling to consider the ionic reaction as being an equilibrium reaction when compared with each charge transfer reaction at the surface of the structural material in point of the reaction rate. Current densities "$ih_n$" (A/cm²) (n=1, 2, 3, 4) shown in FIG. 4 correspond to the reaction rates of the respective reaction steps. Symbols "$kh_n$" (n=1, 2, 3, 4) denote the rate constants (cm/s) of the charge transfer reactions of the respective reaction steps. Letter "M" in FIG. 4 denotes the structural material.

By the way, it does not always hold true that the processes shown in FIG. 3 (Chemical formulae 6 to 10) and in FIG. 4 (Chemical formulae 11 to 18) are the elementary reactions. However, in view of the coincidence, to be stated later, between simulation results and the actually measured values of the corrosion potential, the reaction models employed in this embodiment were sufficiently effective for, at least, the purpose of monitoring the corrosion environment.

The reaction models illustrated in FIG. 3 and FIG. 4 are different from any reaction models having hitherto been proposed, and have been proposed anew this time by the inventors of the present invention.

The quantity "ih" can be obtained by a procedure which is similar to that of the quantity "i". The current "ih" which indicates the overall reaction rate of the charge transfer reaction between hydrogen and a proton, becomes as expressed by the following equation 29:

$$ih = ih_1 + ih_3 - ih_2 - ih_4 \quad \text{[Equation 29]}$$

$$= F[kh_1 C_{Cs} + (kh_3 + kh_2) C_{Ds} - kh_4 C_{Es}]$$

Here, a process in which hydrogen releases an electron to be oxidized into a proton, that is, an anode reaction shall be set positive. In Equation 29, symbol "$Cjs$" denotes the concentration (mol/cm³) of the chemical species "j" at the surface of the structural material. Among the suffixes ("j"), letter C indicates the hydrogen, letter D the intermediate, and letter E the proton.

The surface concentrations $C_{Cs}$, $C_{Es}$ and $C_{Ds}$ contained in Equation 29 can be computed by handling similar to that of the cathode reaction system. The results are as indicated by the following equations 30, 31 and 32:

$$C_{Cs} = [(D_C C_C*/\delta_C) (kh_2 + kh_3 + \quad \text{[Equation 30]}$$

$$D_D/\delta_D)(kh_4 + D_E/\delta_E) + kh_2 kh_4 (1.58 \times$$

$$10^{-9} D_E/\delta_E) - kh_3 kh_4 D_C C_C*/\delta_C]/\Theta \text{ (mol/cm}^3\text{)}$$

$$C_{Ds} = [(1.58 \times 10^{-9} D_E/\delta_E) kh_4(kh_1 + \quad \text{[Equation 31]}$$

$$D_C/\delta_C) + kh_1(D_C C_C*/\delta_C)(kh_4 + D_E/\delta_E)]/\Theta \text{ (mol/cm}^3\text{)}$$

$$C_{Es} = [(1.58 \times 10^{-9} D_E/\delta_E) (kh_1 + \quad \text{[Equation 32]}$$

$$D_C/\delta_C)(kh_2 + kh_3 + D_D/\delta_D) + kh_1 kh_3 D_C C_C*/\delta_C -$$

$$(1.58 \times 10^{-9} D_E/\delta_E) kh_1 kh_2]/\Theta + 1.58 \times 10^{-9} \text{ (mol/cm}^3\text{)}$$

The details of characters and expressions contained in Equations 30, 31 and 32 are as indicated by Equations 33 to 37 below.

$$\Theta = (kh_1 + D_C/\delta_C)(kh_2 + kh_3 + D_D/\delta_D)(kh_4 + \quad \text{[Equation 33]}$$

$$D_E/\delta_E) - kh_3 \, kh_4(kh_1 + D_C/\delta_C) - kh_1 \, kh_2(kh_4 + D_E/\delta_E) \; (\text{cm/s})^3$$

$$kh_1 = kh_1° exp\{\beta_1 F(E-Eh_1°)/RT\} \; (\text{cm/s}) \quad \text{[Equation 34]}$$

$$kh_2 = kh_2° exp\{-(1-\beta_1)F(E-Eh_1°)/RT\} \; (\text{cm/s}) \quad \text{[Equation 35]}$$

$$kh_3 = kh_2° exp\{\beta_2 F(E-EH_2°)/RT\} \; (\text{cm/s}) \quad \text{[Equation 36]}$$

$$kh_4 = kh_2° exp\{-(1-\beta_2)F(E-Eh_2°)/RT\} \; (\text{cm/s}) \quad \text{[Equation 37]}$$

Here, symbols "$\beta_1$" and "$\beta_2$" denote transfer coefficients in the oxidizing directions of the respective reaction steps of the hydrogen/proton charge-transfer reaction system. Symbols "$kh_1°$" (cm/s) and "$kh_2°$" (cm/s) denote the standard rate constants of the respective reaction steps of the same reaction system. Letter E indicates a potential (V) versus the reference electrode. Symbols "$Eh_1°$" and "$Eh_2°$" denote the standard electrode potentials (V) of the respective reaction steps of the aforementioned reaction system. Symbol "$Dj$" denotes the diffusion coefficient (cm$^2$/s) of the chemical species "j". Letters F, R and T respectively indicate ordinary constants.

Next, the quantity "is" contained in Equation 1 will be elucidated.

The quantity "is" which indicates the overall charge-transfer reaction rate of the structural material (stainless steel in this embodiment), has been obtained in the form of a regression curve in such a way that a measured current-potential curve is approximated as the 9th-order function of the potential by the least squares method. The result is Equation 38:

$$is = [7.5973 + 68.052E^{-1} + 305.0.8E^{-2} - \quad \text{[Equation 38]}$$

$$241.97E^{-3} - 3800.9E^{-4} - 2143.6E^{-5} + 17770E^{-6} +$$

$$17681E^{-7} - 28244E^{-8} - 33621E^{-9}]/10^{-6} \; (\text{A/cm}^2)$$

FIG. 5 illustrates the theoretical curve of the current-potential curve for the stainless steel. The correlation coefficient between the measurement data (the approximation curve thereof given by Equation 38) and the theoretical curve is 0.9996.

The quantities "i" (Equation 17), "ih" (Equation 29) and "is" (Equation 38) and the equations (Equations 18 to 28 and Equations 30 to 37) indicative of the details of these quantities as have been obtained above are substituted into Equation 1, and this equation is solved as to the potential E, whereby the corrosion potential E can be computed. As already stated, the equation is solved by the Newton method in this embodiment.

The corrosion potential computation program in the present invention centers on contents which concern the arithmetic processing described above. The electrochemical parameters contained in the computational formula, such as the transfer coefficients, rate constants, diffusion coefficients and standard electrode potentials, are written as constants in the program beforehand.

The thickness $\delta j$ (cm) of the diffusion layer changes in accordance with the flow velocity. It has been ascertained that the relationship between the diffusion layer thickness $\delta j$ and the flow velocity is given by Equation 39 on the basis of the result of Holser et al.'s study (R. A. Holser et al.: "Corrosion", 46, 9, pp. 764–769 (1990)). In this embodiment, Equation 39 is employed as the diffusion layer thickness $\delta j$ which is contained in Equations 17 and 29. Thus, the influence of the flow velocity on the corrosion potential can also be studied.

$$\delta j = 12.64 v^{-0.70} D_j^{0.356} v^{0.344} d^{0.30} \; (\text{cm}) \quad \text{[Equation 39]}$$

Here, letter "v" indicates the flow velocity (cm/s), letter "D" the diffusion coefficient (cm$^2$/s), letter "v" the kinematic viscosity (cm$^2$/s) of the reactor water, letter "d" the diameter of a fluid portion, and letter "j" each chemical species.

The simulation of the corrosion potential was actually carried out by the operation monitoring system of this embodiment.

As the input data (oxygen concentration, hydrogen peroxide concentration, hydrogen concentration, and flow velocity) necessary for the simulation, those explained below were used in this case.

The stagnant part of the reactor water (that is, the central part of the bottom of the reactor pressure vessel 8 in FIG. 1) was set as the objective part of the simulation, and the flow velocity at the stagnant part was assumed to be zero. In the computation program of this embodiment, the growth limit of the diffusion layer was set at $\delta j = 0.05$ (mm) (this growth limit shall be prestored in the program). In such a case where the flow velocity need not be changed for studying the influence thereof (for example, in a case where the flow velocity at the objective part of the simulation is substantially constant at all times and hardly changes), a certain specified value may well be prestored in the program by excluding the flow velocity from the input data.

Used as the oxygen concentration, hydrogen peroxide concentration and hydrogen concentration were the respective concentrations in the bottom of the reactor pressure vessel 8 as obtained on the basis of the detected results of the oxygen concentration sensor 150, hydrogen peroxide concentration sensor 151 and hydrogen concentration sensor 152 installed at the parts of the nuclear reactor, and the computation of the radiolysis of the water.

The computer system 3 runs the above program by receiving such input data. Thus, the corrosion potential at the oxidant concentration on that occasion can be computed. The program is iteratively executed while the oxidant concentration is being changed. Then, the relationship of [oxidant concentration—corrosion potential] can be obtained over the whole concentration range.

Figure 6:
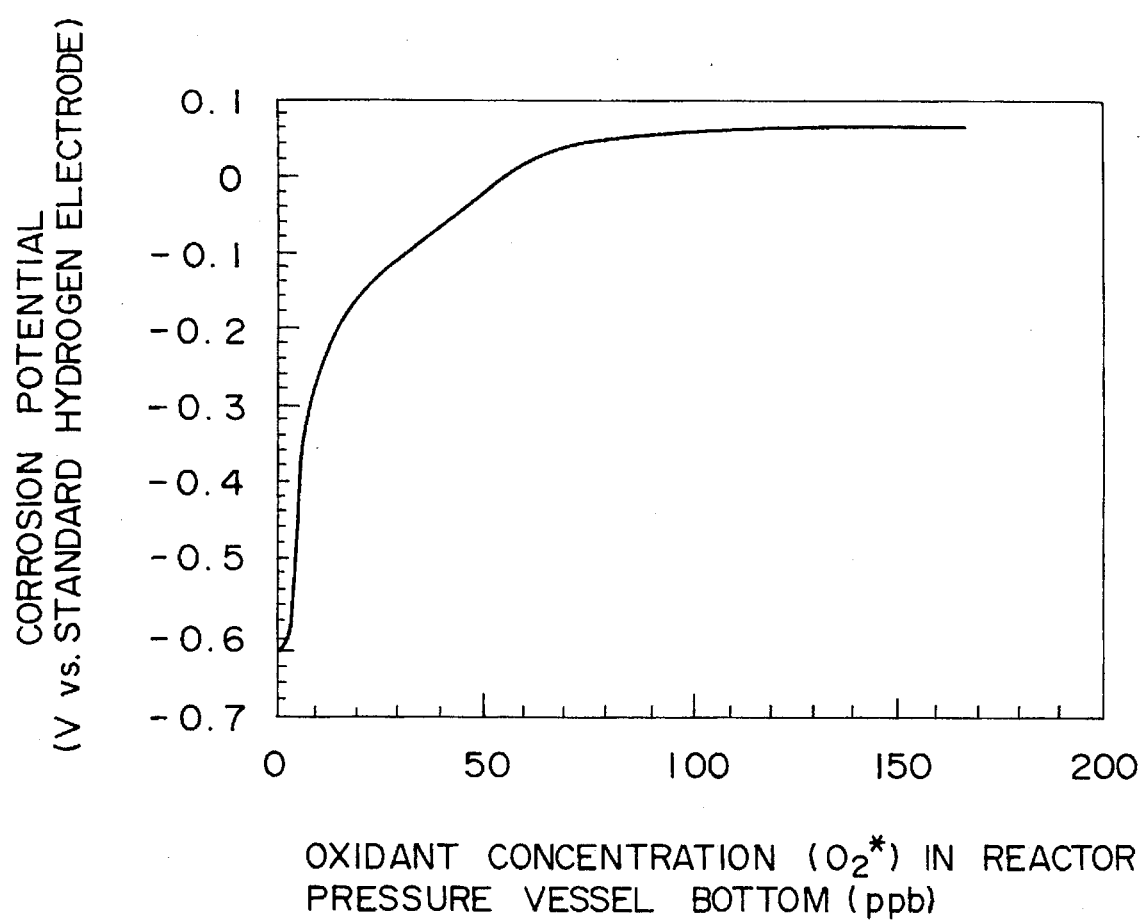
FIG. 6 is a graph showing the relationship between an oxidant concentration in the bottom of the pressure vessel (8) of the light-water nuclear reactor and a corrosion potential, obtained by a simulation.

The simulation result (the relationship between the oxidant concentration and the corrosion potential in the bottom of the reactor pressure vessel 8) is illustrated in FIG. 6. By the way, in this figure, the obtained plots (of the oxidant concentration and the Corrosion potential) are joined to depict a curve. The axis of abscissas in FIG. 6 represents the oxidant concentration ($0_2$*) (in ppb) of the reactor water in the reactor pressure vessel bottom. The "oxidant concentration ($O_2$*)" mentioned here is defined as $$\left( \text{oxygen concentration} + \frac{\text{hydrogen peroxide concentration}}{2} \right)$$

(in ppb). It is a matter of course that the oxygen concentration and hydrogen peroxide concentration to be used in this case are those employed as the input data in the simulation of the corrosion potential.

The oxidant concentration ($0_2$*) changes depending upon the hydrogen concentration of the reactor water which flows through the feed water system 9.

Now, the revealed content of FIG. 6 is applied to the actual operating situation of the nuclear power plant. It is understood that, when the oxidant concentration ($O_2$*) in the bottom of the reactor pressure vessel 8 of the nuclear reactor decreases in correspondence with the hydrogen injection from the hydrogen injector 5, the corrosion potential in the reactor pressure vessel bottom is lowered accordingly.

The threshold value of the stress corrosion cracking of the stainless steel material which is used as the structural material of the nuclear reactor, lies at about −200 (mV) with reference to the potential of the standard hydrogen electrode 1. Considering this point, as a countermeasure for mitigating the corrosion environment, hydrogen may be injected into the feed water system 9 so as to make the oxidant concentration ($O_2^*$) in the bottom of the reactor pressure vessel 8 about 15 (ppb).

Figure 7:
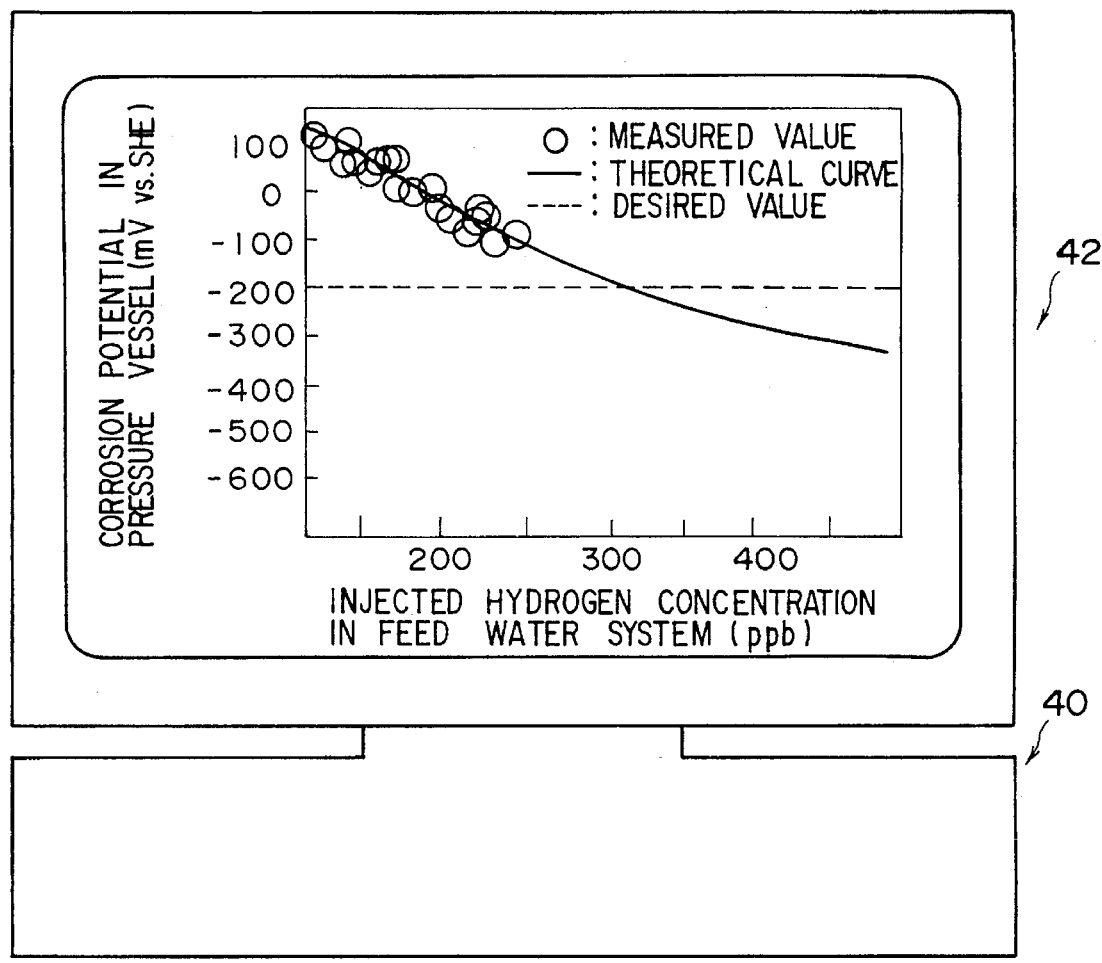
FIG. 7 is a diagram showing an example of a display on a display unit which is arranged in a control room (4) for the reactor.

Further, if the relationship between the oxidant concentration ($O_2^*$) and the amount of injection of hydrogen is known beforehand, the content of FIG. 6 can be more directly illustrated as the relationship between the injected hydrogen concentration and the corrosion potential. The computer system 3 in this embodiment is previously endowed with information which indicates the relationship between the injected hydrogen concentration and the oxidant concentration. Therefore, when the relationship between the oxidant concentration and the injected hydrogen concentration is utilized, the simulation result can be displayed as a graph in which the injected hydrogen concentration is given on the axis of abscissas, while the corrosion potential is given on the axis of ordinates. FIG. 7 illustrates a situation in which the simulation result is drawn on the display screen of the display unit 42 in the control room 4 (and on that of the display unit 35 of the computer system 3). As seen from FIG. 7, a requisite for the consecutive hydrogen injection, which is the countermeasure for mitigating the corrosion environment, is "that the injected hydrogen concentration in the feed water system 9 is held at 300 (ppb)". Accordingly, the operator of the plant (or an automatic controller for the plant) actuates the hydrogen injector 5 in compliance with this requisite.

The display shown 1 in FIG. 7 is more direct and is easier for the operator to understand. Moreover, since the display presents the simulation result (indicated as a theoretical curve by a solid line in FIG. 7) and measured values in superposition, it is effective for confirming this reliabilities etc. Further, the display can prevent the operator from misjudging, owing to the definite indication of a desired value (here, −200 mV). Incidentally, the injected hydrogen concentration represented by the axis of abscissas in the graph of FIG. 7 indicates the set values of the hydrogen injector 5 and does not indicate the measured values of the hydrogen concentration. However, in such a case where the amount of injection of hydrogen is controlled while the hydrogen concentration is being Sequentially detected and confirmed, the measured values of the hydrogen concentration may well be given on the axis of abscissas.

The same content as in the graph of FIG. 7 may well be output from the printer 37 of the computer system 3 or the printer 44 in the control room 4.

By the way, the relationship between the injected hydrogen concentration and the oxidant concentration is obtained by measuring the oxygen concentration and hydrogen peroxide concentration of the reactor water sequentially as the injected hydrogen concentration is changed. Alternatively, it may well be obtained by detecting only the oxygen concentration and executing a predetermined computation. Since methods for the computation have already been put into practical use and have been extensively utilized, they shall not be especially explained here. By way of example, a method disclosed in Japanese Patent Application Laid-open No. 100087/1993 is usable.

The second embodiment of the present invention will now be described.

The first embodiment described before consists in that the relationship between the oxidant concentration (finally, the injected hydrogen concentration) and the corrosion potential is obtained by the simulation. The second embodiment permits further promoting of the above relationship and revealing of the relationship of [oxidant concentration ($O_2^*$)—corrosion potential (simulation result)—propagation rate of stress corrosion cracking (da/dt, measured values)]. That effect of mitigating the stress corrosion cracking which is based on the hydrogen injection, can be studied by revealing the series of relationships. Further, the control (suppression) of the propagation rate of the stress corrosion cracking is permitted by adjusting the oxidant concentration, i.e., the injected hydrogen concentration.

The construction of the second embodiment is basically the same as that of the first embodiment.

Besides the facilities stated in the first embodiment, the computer system 3 in the second embodiment includes a facility for deriving the relationship between the corrosion potential and the propagation rate (da/dt) of the stress corrosion cracking (SCC). This facility is chiefly implemented by running a program stored in the computer system 3.

Figure 8:
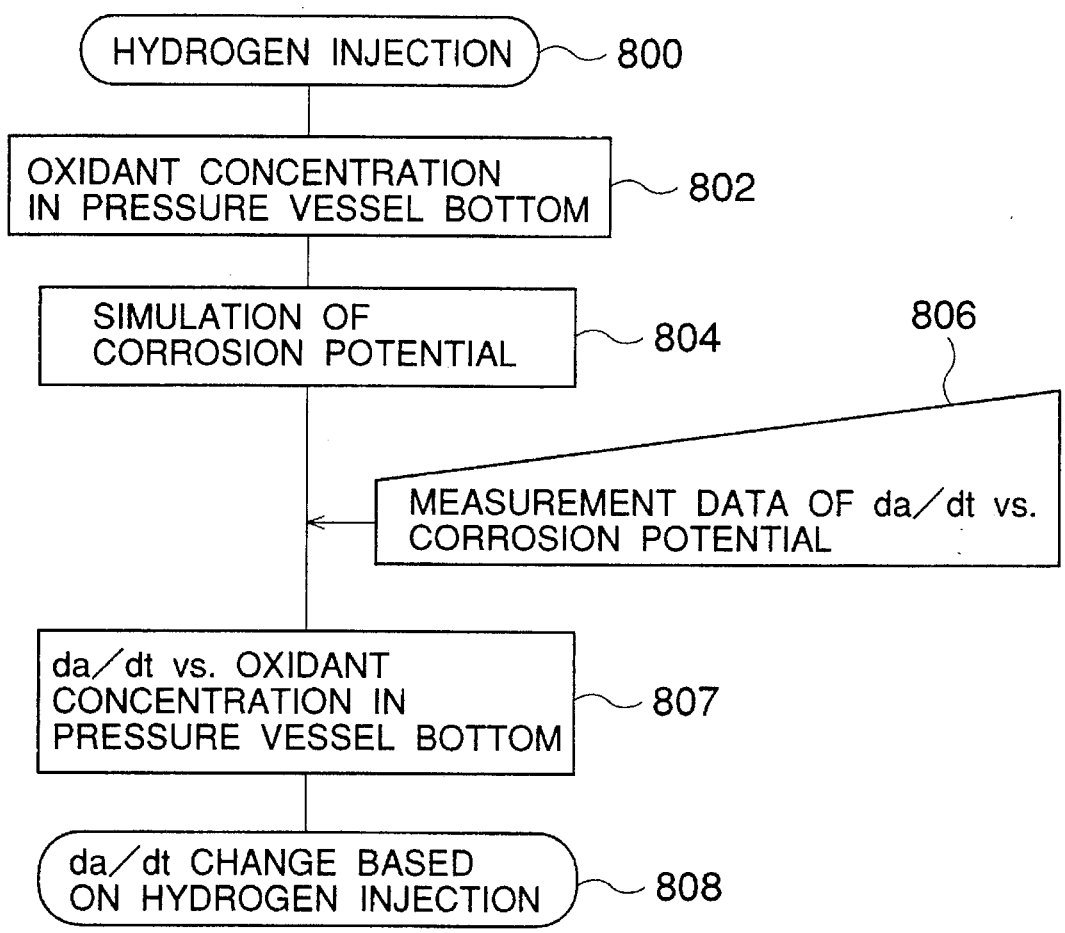
FIG. 8 is a flow chart showing the steps of assessing the effect of hydrogen injection for stress corrosion cracking in the second embodiment of the present invention.

The outline of processing steps for the additional facility is illustrated in FIG. 8 (as a flow for assessing the effect of the hydrogen injection).

First, hydrogen is injected at a certain concentration value (step 800), and the oxidant concentration ($O_2^*$) on this occasion is obtained on the basis of the detected values of the oxygen concentration sensor 150, etc., and predetermined arithmetic processing which uses the detected results (step 802).

Next, a simulation based on the same technique as in the first embodiment is performed to compute the corrosion potential at the value of the oxidant concentration ($_2^*$) on this occasion (step 804).

Subsequently, the relationship between the corrosion potential and the propagation rate (da/dt) of the stress corrosion cracking is found by an experiment, and an experimental formula in which this relationship is formulated is obtained (step 806). Incidentally, experimental data required in this case are prepared separately and are contained in the external memory 33 of the computer system 3 beforehand. Alternatively, it is allowed to separately determine an experimental formula and include only the experimental formula in the program beforehand.

Thereafter, the relationship of [oxidant concentration—corrosion potential] obtained at the step 804 is substituted into the experimental formula which indicates the relationship of [corrosion potential—propagation rate of stress corrosion cracking] obtained at the step 806 (step 807). Thus, the propagation rate of the stress corrosion cracking at the certain value of the oxidant concentration ($O_2^*$) can be found.

Besides, since the injected hydrogen concentration corresponding to the value of the oxidant concentration ($O_2^*$) on this occasion is known (refer to the step 802), the substitution of the corresponding relationship makes it possible to find the stress corrosion cracking propagation rate corresponding to the value of the injected hydrogen concentration on this occasion (step 808).

When the above processing is iteratively executed, the corresponding relationship of [oxidant concentration—propagation rate of stress corrosion cracking] can be obtained over the whole oxidant concentration range.

Since the corrosion potential and the oxidant concentration ($O_2^*$) have a predetermined relationship, the relationship of "the oxidant concentration ($O_2^*$) vs. the stress corrosion cracking propagation rate (da/dt)" is equivalent to that of "the corrosion potential vs. the stress corrosion cracking propagation rate (da/dt)".

Figure 9:
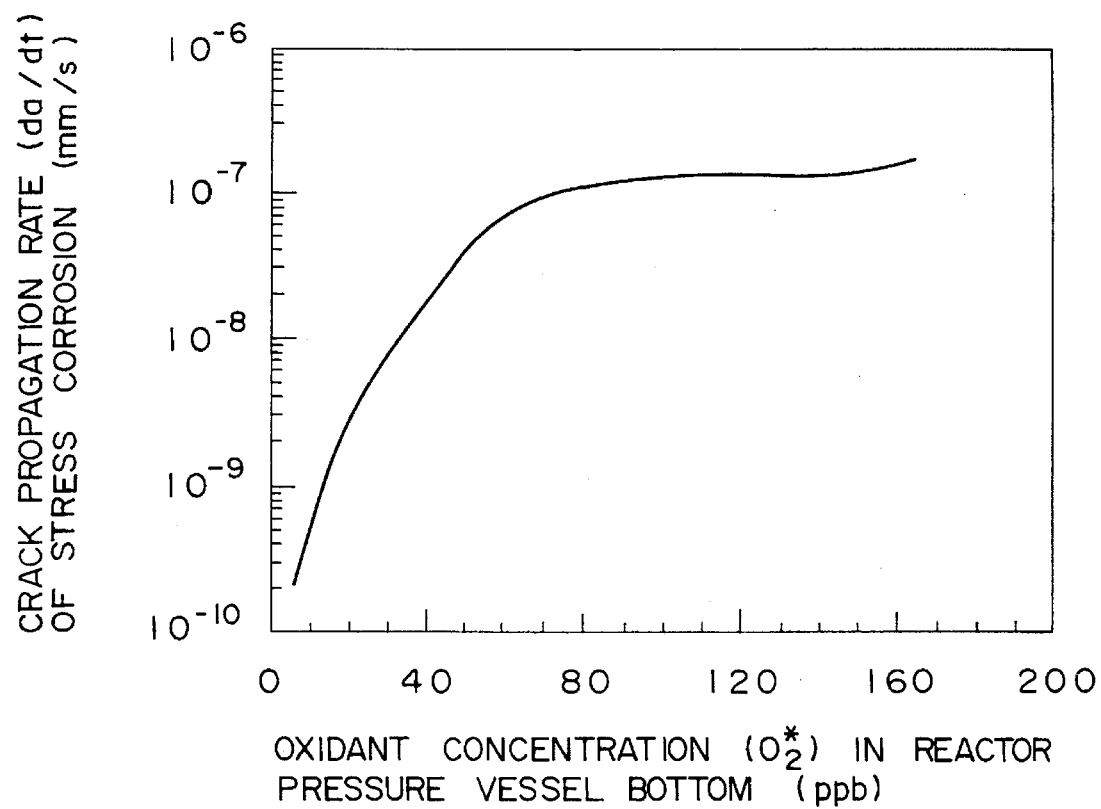
FIG. 9 is a graph showing the relationship between an oxidant concentration and the crack propagation rate of stress corrosion in the bottom of the pressure vessel (8) of the light-water nuclear reactor (in FIG. 1)

The relationship of [oxidant concentration ($O_2^*$)—stress corrosion cracking propagation rate (da/dt)] or [injected hydrogen concentration—stress corrosion cracking propagation rate (da/dt)] obtained by such steps is displayed on the screens of the display units 35 and 42. By way of example, FIG. 9 illustrates a situation in which the relationship of [oxidant concentration ($O_2^*$)—stress corrosion cracking propagation rate (da/dt)] is displayed. Here, the relationship of the stress corrosion cracking propagation rate with the oxidant Concentration has been obtained in the bottom of the reactor pressure vessel 8. The oxidant concentration ($O_2^*$) having a value of about 160 (ppb) corresponds to the state in which the hydrogen injection into the reactor water is not performed. As the value of the oxidant concentration; ($O_2^*$) is smaller than, the aforecited value, the injected hydrogen concentration is higher. In the graph of FIG. 9, plots obtained by the processing explained before are joined so as to be depicted as a curve.

As seen from FIG. 9, in a region in which the oxidant concentration ($O_2^*$) is below about 80 (ppb), the crack propagation rate (da/dt) of the stress corrosion lowers with the oxidant concentration ($O_2^*$). Besides, when the oxidant concentration ($O_2^*$) is 20 (ppb) or so, the propagation rate (da/dt) of the stress corrosion cracking becomes two orders lower than in the state in which the oxidant concentration ($O_2^*$) is about 160 (ppb), that is, in which the hydrogen injection is not performed.

As already explained, the relationship between the injected hydrogen concentration and the oxidant concentration ($O_2^*$) in the bottom of the reactor pressure vessel 8 is known beforehand. In the example of this embodiment, the oxidant concentration ($O_2^*$) in the reactor pressure vessel bottom becomes about 20 (ppb) in a case where the injected hydrogen concentration in the feed water system 9 is at a level of 250 (ppb). It is accordingly understood that the corrosion environment mitigating effect against the stress corrosion cracking in the reactor pressure vessel bottom can be satisfactorily expected by performing a control so as to bring the injected hydrogen concentration in the feed water system 9 to the level of 250 (ppb). When the relationship of [injected hydrogen concentration—stress corrosion cracking propagation rate (da/dt)] obtained at the step 808 in FIG. 8 is displayed by the display unit 42, etc., conveniently the effect with reference to the injected hydrogen concentration can be studied more directly.

The third embodiment of the present invention will now be described.

In the first embodiment, Equation 1 is defined as the equation including the five variables (potential, oxygen concentration, hydrogen peroxide concentration, hydrogen concentration and flow velocity), in such a way that the formulae derived on the basis of the reaction models are respectively substituted into the terms "i" and "ih" among the three terms ("i", "ih" and "is") contained in Equation 1, while the formula obtained by formulating the measurement data (refer to FIG. 4) is substituted into the term "is". Herein, the potential is found by affording the oxygen concentration, hydrogen peroxide concentration, hydrogen concentration and flow velocity as the input data to the defined equation.

On the other hand, the third embodiment defines Equation 1 as an equation whose variables are the oxygen concentration, hydrogen peroxide concentration, hydrogen concentration, flow velocity, current "is" and corrosion potential, in such a way that the relationship of [oxygen concentration, etc.—corrosion potential] obtained as measurement data is substituted into the terms "i" and "ih" of Equation 1. Herein, the relationship between the current "is" and the corrosion potential is found by affording the oxygen concentration, hydrogen peroxide concentration, hydrogen concentration and flow velocity as input data to the defined equation.

An operation monitoring system in this embodiment can be implemented by altering the processing contents which the computer system 3 executes. The hardware architecture of the operation monitoring system is the same as in the first embodiment. Accordingly, the ensuing description shall be centered on the processing contents of the computer system 3.

Figure 10:
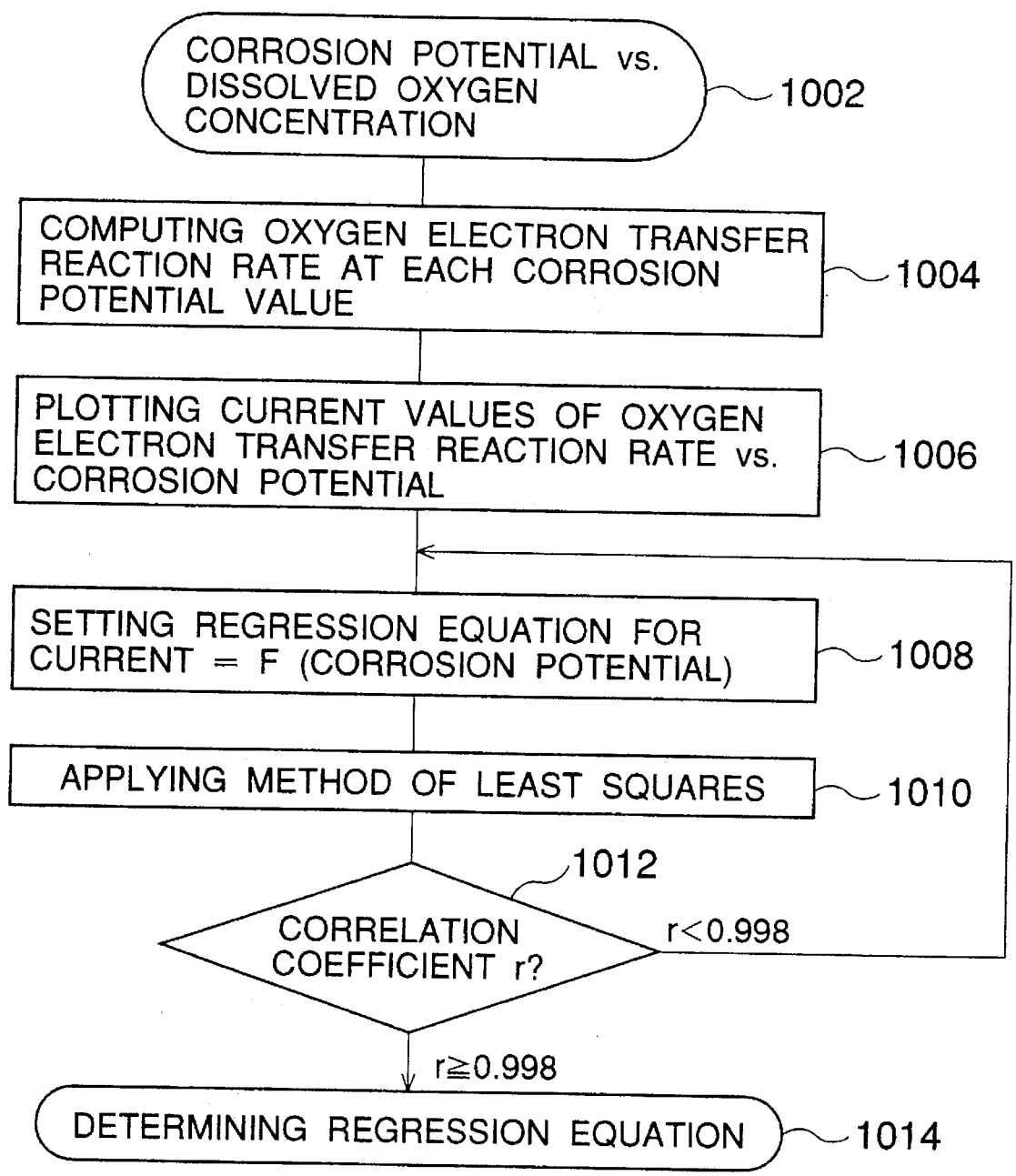
FIG. 10 is a flow chart showing the steps of determining the current-potential curve of a material from measured corrosion potential data in the third embodiment of the present invention.

The processing steps of a flow for formulating a current-potential curve will be concretely explained below in conjunction with FIG. 10.

In an example taken here, only a dissolved oxygen concentration was employed as the parameter indicative of the water chemistry or quality in order to simplify the explanation. Since, in this case, neither hydrogen nor hydrogen peroxide exists, a relational equation concerning the corrosion potential is expressed by the following equation 40:

$$i = is \qquad \text{[Equation 40]}$$

The relationship between the oxygen concentration and the corrosion potential is measured beforehand (step 1002).

Subsequently, measurement data obtained at the step 1002 are substituted into the quantity "i" of Equation 40 (since only the oxygen concentration is set as the parameter here, the quantity "i" in this case corresponds to only the term containing $C_{As}$ in Equation 3), whereby the relationship between the corrosion potential and the current "is" can be obtained (step 1004). The quantity "i" in this case is input to the computer under the condition of (the initial concentration of hydrogen peroxide)=0.

Subsequently, the relationship between the corrosion potential and the current "is" as obtained at the step 1004 is plotted on a graph (step 1006). Further, a regression curve for expressing the plotted data as an approximate formula is obtained. Here in this example, the least squares method was employed. Also, a regression equation determining condition was set at 0.998 or above in terms of a correlation coefficient. (Refer to steps 1008 to 1014.)

Actually, the above processing is done by the computer system 3.

Even in a case where hydrogen, hydrogen peroxide, etc. coexist, the current-potential curve can be obtained by fundamentally the same steps.

The current-potential curve of stainless steel obtained by the above steps is displayed on the screens of the display unit 42, etc. An example of the display is illustrated in FIG. 11.

The measurement data substituted into Equation 40 in the case of obtaining the current-potential curve shown in FIG. 11, were on a test piece which was formed with a film for a long time period under the conditions of a dissolved oxygen concentration level of 200 (ppb) and a temperature of 288 (°C.).

The regression equation "is'" of the current-potential curve in FIG. 11 has been obtained as the following equation 41:

$$is' = [5.7494 + 92.165E^{-1} + 697.80E^{-2} - \quad \text{[Equation 41]}$$
$$33.766E^{-3} - 27695E^{-4} - 98538E^{-5} + 281450E^{-6} +$$
$$2.4101*10^{-6}E^{-7} + 5.2267*10^{-6}E^{-8} + 3.8441*10^{-6}E^{-9}]/10^{-6} \, (A/cm^2)$$

The correlation coefficient between Equation 41 and the current-potential computation data is 0.9999.

The current-potential curve (FIG. 11, Equation 41) and obtained by the method explained in the third embodiment is different from the measured current-potential curve (FIG. 5, Equation 38) indicated in the first embodiment. This is because test pieces handled were originally different. More specifically, the current-potential curve in FIG. 5 was obtained on the basis of the measurement data concerning the test piece in which a surface oxidation film did not grow sufficiently. On the other hand, the current-potential curve in FIG. 11 was obtained on the basis of the data concerning the test piece in which the film was formed for the long time period as stated above.

The test piece whose current-potential curve ought to be used as the input data in the corrosion potential simulation, needs to be judged from the surface state etc. of the objective material of the simulation. By way of example, in a case where the test piece of the stainless steel is inserted into the actual plant and where the corrosion environment mitigating effect based on the hydrogen injection or the like is studied, the current-potential curve concerning the test piece in which the oxide film is not sufficiently grown should preferably be used as the input data. On the other hand, in a case where the corrosion potential of the material of the actual plant is, in itself, to be discussed, the current-potential curve concerning the material in which the oxide film is sufficiently grown and pretreated should preferably be used as the input data.

In order to actually measure the current-potential curve, the current must be actually caused to flow. It is difficult, however, to accurately measure the current. It is therefore very significant that, as in this embodiment, the current-potential curve is obtained on the basis of the experimental data acquired in the state in which no current is caused to flow, in other words, that the information (current-potential curve) indicative of a nonequilibrium state are derived using the data in the equilibrium state. The current-potential curve obtained with the technique of the third embodiment can also be used as the input data in the case of measuring the corrosion potential by the simulation in the first embodiment.

Figure 12:
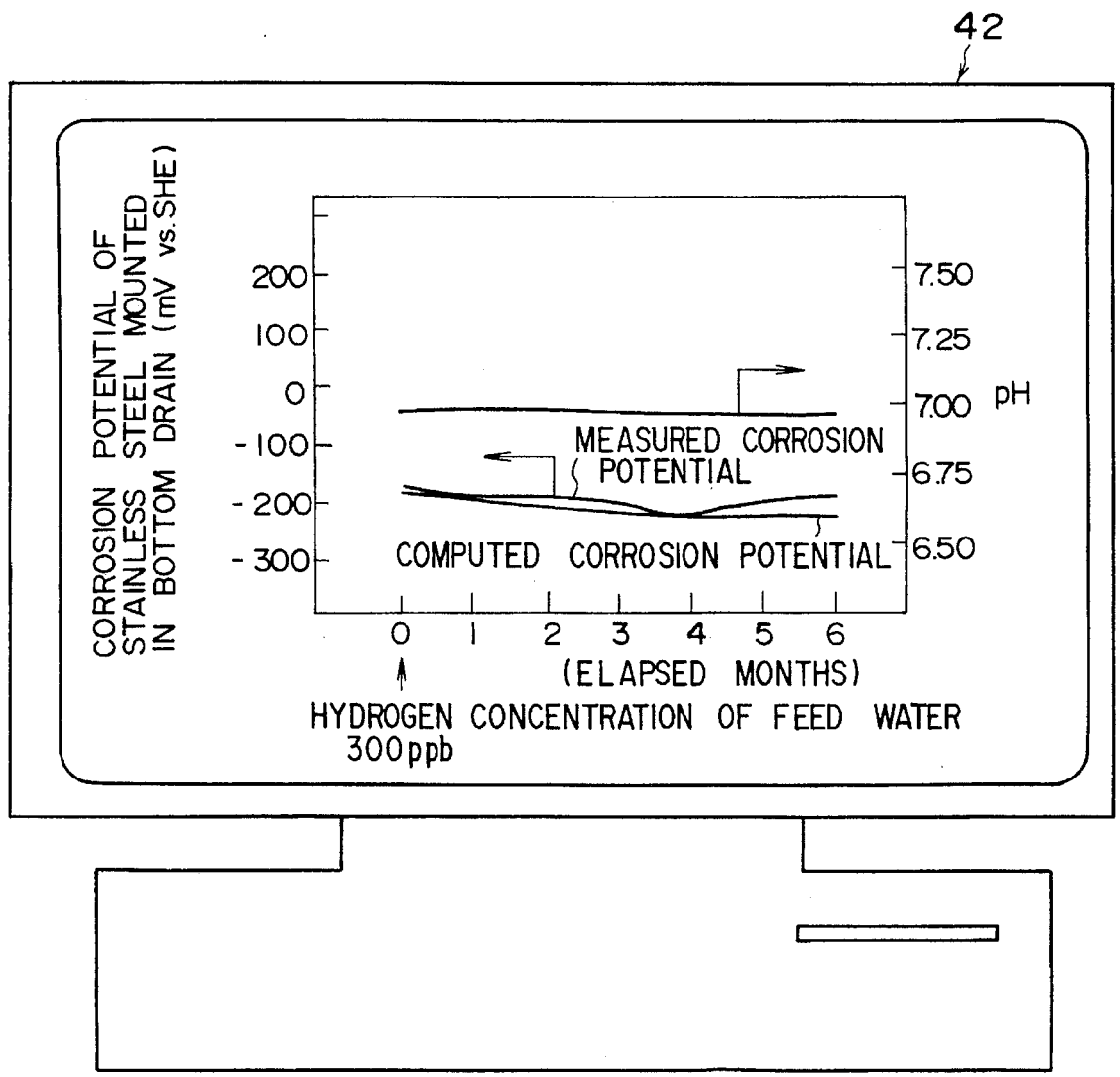
FIG. 12 is a diagram showing the situation of the display of the time-based changes of the corrosion potentials and the pH of reactor water.
Figure 13:
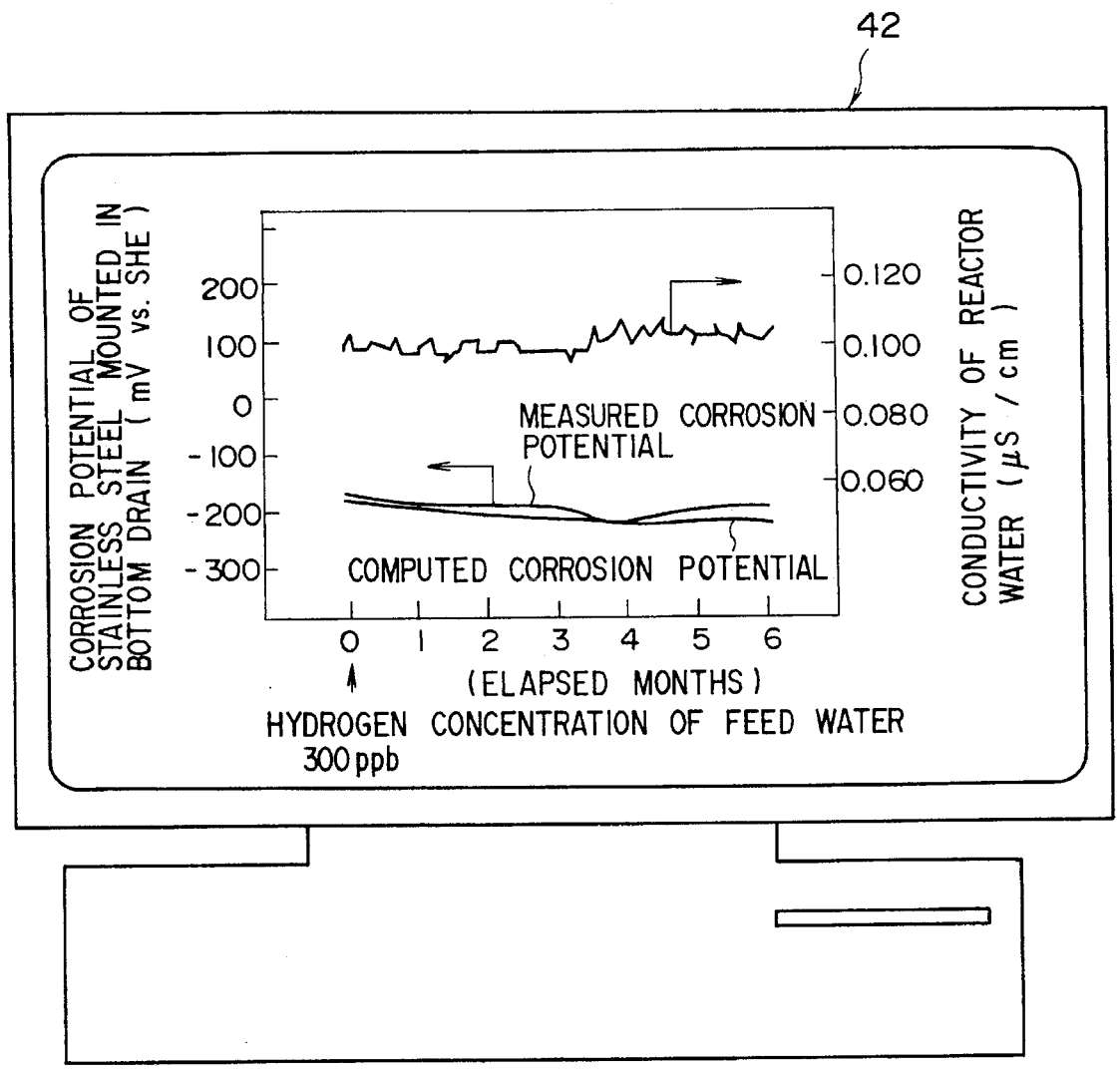
FIG. 13 is a diagram showing the situation of the display of the time-based changes of the corrosion potentials and the electric conductivity of the reactor water.

Data which demonstrate the effectiveness of the first embodiment, are exemplified in FIGS. 12 and 13.

FIG. 12 displays the time-based change of the corrosion potential for six months, together with that of the pH of the reactor water. Regarding the corrosion potential, the measured values of the corrosion potential of stainless steel located in the bottom drain pipe 12 as have been obtained in Case of holding the hydrogen concentration in the feed water system 9 at 300 (ppb) are indicated by a bold line, and the simulation result of the corrosion potential under the same conditions is indicated by a fine line. The pH values displayed here are results measured by the pH sensor 152. Incidentally, the measurement was conducted by sampling each test piece and thereafter cooling it near to the room temperature. On the other hand, FIG. 13 displays the time-based change of the corrosion potential for six months, together with that of the electrical conductivity of the reactor water. The displayed corrosion potential is the same as in FIG. 12.

In the light of FIGS. 12 and 13, the computed corrosion potential and the measured corrosion potential agree at a satisfactory level in practical use, and the effectiveness of the present invention has been verified. Moreover, the operator can confirm that the water quality and the injection state of hydrogen have been held constant in the meantime, by watching the change of the pH or the electric conductivity which is simultaneously displayed.

In this manner, the operating state of the plant can be comprehensively monitored by conjointly displaying the different information on the screen of the display unit 42. Besides, whether or not the basic control has been reliably performed can be simultaneously known, so that a cause can be found more easily when any abnormality in the corrosion potential has been noted. Further, since various items of information can be obtained at one time without renewing the display of the screen, the monitoring of the operating state is facilitated. In the nuclear power plant, the other information items to be displayed are, for example, the measured potential of an inactive metal (platinum), information on the radioactive nitrogen contained in the main steam, information on the cracking propagation, and the radiation dose rate of the main steam system.

In the foregoing embodiments, the "specified substance" mentioned in the appended claims corresponds to each of oxygen, hydrogen peroxide and hydrogen. The "environment index" corresponds to the oxidant concentration ($O_2^*$). The "specified operation" corresponds to the injection of hydrogen.

Also, the "output unit" mentioned in the appended claims corresponds to each of the display units 35, 42 and printers 37, 44 of the computer system 3 and control room 4 in the foregoing embodiments. The "arithmetic and control unit" corresponds to the CPU 30 of the computer system 3, or the like. The "memory unit" corresponds to the external memory 33, or the like. It is to be understood, however, that the constituent units demonstrate their functions in close association with one another, and that the individual corresponding relations are not strict.

The present invention does not have its application restricted to the nuclear power plant, but it is extensively applicable to other plants. Besides, the material whose potential is to be computed may be any pure metal or any alloy (for example, stainless steel, a nickel-based alloy, or carbon steel).

In each of the embodiments described above, the information items up to the rate determining steps which determine the reaction rates of the oxidizing and reducing reactions are modeled by dividing the charge transfer reaction at one or more elementary reaction levels. Thus, it has been permitted to compute the corrosion potential with the actual corrosion reaction mechanism as a background. Therefore, the credibility of the obtained corrosion potential is high.

According to the present invention, it has become possible to replace the rate of the corrosion reaction of the material with the current-potential relationship by the use of the measured corrosion potential data. In general, the measurement of a current-potential curve necessitates a large amount of supporting electrolyte, and it is liable to inevitably perform a measurement under conditions different from those of an actual corrosion environment. The corrosion potential measurement is performed in the equilibrium state, and it has usually been done in the actual environment. According to the present invention, it has also become possible for the corrosion rate in the in-situ environment to be expressed as the current-potential relationship on the basis of the unprocessed corrosion potential information.

The present invention has permitted the theoretical assessment which centers on the corrosion potential, and which is necessary for the water quality control of the actual plant. Thus, it becomes possible to enhance the precision and reliability of the operation management system for the plant. Concretely, indispensable technical information can be acquired in, for example, a case where the amount of injection of hydrogen is determined by studying the injection effect of the hydrogen injection into the plant.

According to the present invention, advantages to be stated below are obtained.

It is possible to simulate a corrosion potential on the basis of handling which conforms to an actual reaction. Moreover, the corrosion potential can be known by the simulation even at a part which is actually unmeasurable. Accordingly, a corrosion environment mitigating effect based on hydrogen injection or the like, the change of the propagation rate of stress corrosion cracking, etc. can be theoretically studied on the basis of the corrosion potential. That is, the operating conditions of a plant can be determined after theoretically studying them from the viewpoint of corrosion environment mitigation. Therefore, a plant operation of high accuracy and high reliability is realized.

Further, the current-potential curve of a corrosion reaction which is difficult to actually measure (the potential characteristics of a reaction rate) can be obtained by a computation.

What is claimed is:

1. A plant monitoring system for monitoring a plant including a sensor for detecting a concentration of at least one species of a certain specified substance existing within the plant, comprising:

a memory unit storing therein a formula of a relationship between a corrosion rate and a corrosion potential that is derived from at least two reaction rate equations relevant to at least one reaction process model indicating at least two steps of consecutive elementary electrochemical reaction processes in which the specified substance participates within said plant, and information on a reaction rate of a reaction that is taking place with respect to a structural material of said plant;

an arithmetic and control unit which computes a potential of the structural material by using the formula and the information on the reaction rate stored in said memory unit, and the concentration of said specified substance detected by said sensor; and an output unit for delivering the potential of said structural material computed by said arithmetic and control unit.

2. A plant monitoring system as defined in claim 1, wherein the specified substances are oxygen, hydrogen peroxide and hydrogen.

3. A plant monitoring system as defined in claim 1, wherein said information on said reaction rate of said reaction which might be taking place with respect to said structural material of said plant is information which indicates a current-potential relationship concerning said reaction.

4. A plant monitoring system as defined in claim 1, wherein the reaction process model contains hydrogen peroxide as an intermediate.

5. A plant monitoring system as defined in claim 1, wherein the reaction process includes a reaction in which hydrogen peroxide is decomposed and/or formed in accordance with at least two steps of consecutive elementary electrochemical reaction processes and a chemical reaction process model.

6. A plant monitoring system as defined in claim 1 further including a stress corrosion cracking sensor.

7. A plant monitoring system as defined in claim 1, wherein said reaction rate equations include an equation of a charge transfer reaction rate.

8. A plant monitoring system as defined in claim 1 further comprising an apparatus for injecting hydrogen, and control means for controlling the amount of hydrogen injected in accordance with said potential of said structural material.

9. A plant monitoring system as defined in claim 1, wherein said elementary electrochemical reaction processes includes following consecutive reactions (a) through (e):

(a) $O_2 + 2H^+ + 2e \rightarrow H_2O_2$ (b) $H_2O_2 \rightarrow O_2 + 2H^+ + 2e$ (c) $H_2O_2 + 2H^+ + 2e \rightarrow 2H_2O_2$ (d) $H_2O_2 \rightarrow (\frac{1}{2})O_2 + 2H_2O_2$ (decomposition in bulk solution)

(e) $H_2O_2 \rightarrow (\frac{1}{2})O_2 + 2H_2O_2$ (surface catalytic decomposition).

10. A plant monitoring system as defined in claim 1, wherein:

said reaction process model is a model of a corrosion reaction process indicating at least two steps of consecutive elementary electrochemical reaction processes;

said reaction rate is a reaction rate of the corrosion reaction that is taking place with respect to the structural material;

said concentration is a concentration of the substance participating in the corrosion reaction that is taking place with respect to the structural material; and said arithmetic and control unit computes a potential as the corrosion potential at which reaction rates of an anode reaction and a cathode reaction included in the corrosion reaction become equal, through a numerical analysis on the basis of an electrochemical mixed-potential theorem by using said formula, said information, and said concentration.

11. A plant monitoring system as defined in claim 10 wherein said plant is a nuclear power plant and wherein one of the at least two reaction rate equations is an equation of a charge transfer reaction rate including concentrations of oxygen and hydrogen peroxide at a surface of said material.

12. A plant monitoring system as defined in claim 10, wherein said plant is a nuclear power plant, and wherein one of the at least two reaction rate equations is an equation of a charge transfer reaction rate including a concentration of hydrogen at a surface of said material, a concentration of protons at the surface of said material, and a concentration of atomic-state hydrogen absorbed by said material.

13. A plant monitoring system for monitoring a plant, comprising:

a sensor for detecting a concentration of at least one species of certain specified substance existing within said plant;

a memory unit which stores therein a formula of a relationship between a corrosion rate and a corrosion potential that is derived from at least two reaction rate equations relevant to at least one reaction process model indicating at least two steps of consecutive elementary electrochemical reaction processes in which the specified substance participates within said plant, and information on a reaction rate of a reaction that is taking place with respect to a structural material of said plant;

an arithmetic and control unit which computes a potential of the structural material by using the reaction rate equations and the information on the reaction rate stored in said memory unit, and the concentration of said specified substance detected by said sensor; and an output unit for delivering the potential of said structural material computed by said arithmetic and control unit.

14. A plant system comprising:

a vessel in which a reaction is conducted;

a sensor for detecting a concentration of at least one species of a certain specified substance existing under an environment within said vessel;

a memory unit for storing therein a formula of a relationship between a corrosion rate and a corrosion potential reflective of at least two reaction rate equations derived in accordance with models of at least two steps of consecutive reaction processes in which the specified substance seems to participate in occurrence of the reaction process under the environment, and information on a reaction rate of a reaction that might be taking place with respect to a structural material of said vessel;

an arithmetic and control unit for computing a potential of the structural material by using the formula reflective of the reaction rate equations and the information on the reaction rate stored in said memory unit, and the concentration of said specified substance detected by said sensor; and an output unit for delivering the potential of said structural material computed by said arithmetic and control unit.

* * * * *